(12) United States Patent
Sarin et al.

(10) Patent No.: US 12,059,533 B1
(45) Date of Patent: Aug. 13, 2024

(54) DIGITAL MUSIC THERAPEUTIC SYSTEM WITH AUTOMATED DOSAGE

(71) Applicant: Pineal Labs Inc., Pacific Palisades, CA (US)

(72) Inventors: Neal Sarin, Pacific Palisades, CA (US); Warren Riker, Rotunda West, FL (US)

(73) Assignee: Pineal Labs Inc., Pacific Palisades, CA (US)

( * ) Notice: Subject to any disclaimer, the term of this patent is extended or adjusted under 35 U.S.C. 154(b) by 0 days.

(21) Appl. No.: 18/111,497

(22) Filed: Feb. 17, 2023

Related U.S. Application Data

(63) Continuation-in-part of application No. 17/481,152, filed on Sep. 21, 2021, now abandoned, which is a
(Continued)

(51) Int. Cl.
| | |
|---|---|
| *A61M 21/02* | (2006.01) |
| *A61M 21/00* | (2006.01) |
| *G10H 1/00* | (2006.01) |
| *G10L 15/22* | (2006.01) |
| *G10L 25/66* | (2013.01) |

(Continued)

(52) U.S. Cl.
CPC .......... *A61M 21/02* (2013.01); *G10H 1/0025* (2013.01); *G10L 15/22* (2013.01); *G10L 25/66* (2013.01); *G16H 10/20* (2018.01); *G16H 20/70* (2018.01); *A61M 2021/0027* (2013.01); *A61M 2021/005* (2013.01); *A61M 2205/505* (2013.01); *A61M 2205/52* (2013.01); *A61M 2205/583* (2013.01); *G10H 2210/111* (2013.01);
(Continued)

(58) Field of Classification Search
None
See application file for complete search history.

(56) References Cited

U.S. PATENT DOCUMENTS

| | | |
|---|---|---|
| 5,135,468 A | 8/1992 | Meissner |
| 5,289,438 A | 2/1994 | Gall |
| | (Continued) | |

OTHER PUBLICATIONS

Barthet, Mathieu et al., "Music Emotion Recognition: From Content to Context-Based Models", Jan. 2013, pp. 1-25.
(Continued)

*Primary Examiner* — Jianchun Qin
(74) *Attorney, Agent, or Firm* — Raubvogel Law Office

(57) ABSTRACT

Musical compositions and/or other audio programs are automatically identified, generated, curated, and/or personalized, so as to treat, mitigate, and/or address specific symptoms, such as those related to mental health disorders. Based on a user's particular issues relating to poor sleep, stress, anxiety, and/or other conditions, particular audio programs are automatically output so as to alleviate and/or address such issues. The system uses metadata to automatically identify, generate, curate, and/or personalize musical compositions and/or other audio programs, and to match such programs with particular conditions and issues, so as to maximize effectiveness in addressing such issues in users. In at least one embodiment, the system may automatically determine, based on survey responses indicating the severity of the user's symptoms, a dosage for audio programs to be output for the user, and may set a time to automate the amount of time the user listens to the audio programs.

30 Claims, 14 Drawing Sheets

Related U.S. Application Data continuation-in-part of application No. 16/914,159, filed on Jun. 26, 2020, now abandoned, which is a continuation-in-part of application No. 16/879,580, filed on May 20, 2020, now abandoned.

(51) Int. Cl.
*G16H 10/20* (2018.01)
*G16H 20/70* (2018.01)

(52) U.S. Cl.
CPC . *G10H 2210/305* (2013.01); *G10H 2210/315* (2013.01); *G10H 2210/391* (2013.01); *G10H 2220/101* (2013.01)

(56) References Cited

U.S. PATENT DOCUMENTS

| | | | |
|---|---|---|---|
| 6,135,944 A | 10/2000 | Bowman et al. | |
| 6,506,969 B1 | 1/2003 | Baron | |
| 7,141,028 B2 | 11/2006 | McNew | |
| 7,968,785 B2 | 6/2011 | Howarth | |
| 8,244,546 B2 | 8/2012 | Nakano et al. | |
| 8,708,705 B1 | 4/2014 | Baker et al. | |
| 8,734,317 B2 | 5/2014 | Sperling et al. | |
| 9,489,938 B2 | 11/2016 | Mizuguchi et al. | |
| 9,839,762 B2 | 12/2017 | Berg et al. | |
| 9,886,965 B1 | 2/2018 | Ahmet et al. | |
| 10,325,581 B2 | 6/2019 | Ogasawara | |
| 10,431,193 B2 | 10/2019 | Setoguchi | |
| 10,497,347 B2 | 12/2019 | Ogasawara | |
| 10,529,312 B1 | 1/2020 | Adams et al. | |
| 10,587,967 B2* | 3/2020 | Osborne | G16H 20/70 |
| 10,629,179 B2 | 4/2020 | Danjyo et al. | |
| 2004/0006472 A1 | 1/2004 | Kemmochi | |
| 2007/0137463 A1 | 6/2007 | Lumsden | |
| 2009/0306987 A1 | 12/2009 | Nakano et al. | |
| 2010/0024626 A1 | 2/2010 | Howarth | |
| 2010/0056854 A1* | 3/2010 | Chang | A61M 21/00 600/28 |
| 2010/0208631 A1 | 8/2010 | Zhang et al. | |
| 2011/0004476 A1 | 1/2011 | Saino et al. | |
| 2011/0054902 A1 | 3/2011 | Li et al. | |
| 2013/0019738 A1 | 1/2013 | Haupt et al. | |
| 2013/0151256 A1 | 6/2013 | Nakano et al. | |
| 2014/0006031 A1 | 1/2014 | Mizuguchi et al. | |
| 2014/0046667 A1 | 2/2014 | Yeom et al. | |
| 2015/0025892 A1 | 1/2015 | Lee et al. | |
| 2015/0356876 A1 | 12/2015 | Wang et al. | |
| 2016/0157464 A1 | 6/2016 | Levi et al. | |
| 2017/0026747 A1 | 1/2017 | Scroggins | |
| 2017/0027168 A1 | 2/2017 | Heath | |
| 2017/0087364 A1* | 3/2017 | Cartledge | A61N 1/36034 |
| 2019/0059326 A1 | 2/2019 | Levi et al. | |
| 2019/0189259 A1 | 6/2019 | Clark | |
| 2019/0209805 A1 | 7/2019 | Ra Speret | |
| 2019/0225521 A1 | 7/2019 | Death | |
| 2019/0298966 A1 | 10/2019 | Mawson | |
| 2019/0335712 A1 | 11/2019 | Levi et al. | |
| 2019/0378531 A1 | 12/2019 | Jensen et al. | |
| 2019/0385578 A1 | 12/2019 | Yang | |
| 2020/0005744 A1 | 1/2020 | Godunov | |
| 2020/0077939 A1 | 3/2020 | Richer et al. | |
| 2020/0094066 A1 | 3/2020 | Heath | |
| 2020/0101260 A1 | 4/2020 | Santoro | |
| 2020/0105244 A1 | 4/2020 | Kuramitsu et al. | |
| 2020/0113513 A1 | 4/2020 | Hirano et al. | |
| 2020/0243055 A1 | 7/2020 | Grace | |
| 2020/0286456 A1 | 9/2020 | Sarin et al. | |
| 2020/0324076 A1 | 10/2020 | Sarin et al. | |
| 2022/0181004 A1* | 6/2022 | Zilca | G16H 20/70 |
| 2022/0344030 A1* | 10/2022 | Abbas | A61B 5/7267 |
| 2023/0023092 A1* | 1/2023 | Londesbrough | A61K 31/4045 |

OTHER PUBLICATIONS

Basar E., "Brain Function and Oscillations", Brain Oscillations, Principles and Approaches, Springer Science & Business Media, 2012.

Lutz et al., "Cognitive Emotional Interactions: Attention Regulation and Monitoring in Meditations", Trends in Cognitive Sciences, vol. 12, Issue 4, Apr. 2008, pp. 163-169.

PowerThoughts Meditation Club (www.youtube.com/watch?v=OHFdClrwBal).

CORC "Generalised Anxiety Disorder Assessment (GAD-7)", retrieved on Mar. 25, 2023 from https://www.corc.uk.net/outcome-experience-measures/generalised-anxiety-disorder-assessment-gad-7.

* cited by examiner

|  | 302A | 302B | 302C | 302D |
|---|---|---|---|---|
|  | BEFORE MUSIC | | AFTER MUSIC | |
|  | Control Group | Experimental Group | Control Group | Experimental Group |
| Emotional Motivation | 6.4 | 6.1 | 6.3 | 6.0 |
| Memory Activation | 5.7 | 5.7 | 5.3 | 6.0 |
| Attention Processing | 6.2 | 6.6 | 7.1 | 6.2 |

Results are summarized and reported on a 10-pt. scale with an overall score difference of 0.4 being meaningful.

*FIG. 3*

| Artist name | Track name | | Symptoms | Album | Album Artwork | Key | BPM | Instruments | Time of Day | Year |
|---|---|---|---|---|---|---|---|---|---|---|
| cozmoe | Make | | Severe | xyz | img.png | C# | 30 | Piano, Guitar | 6am-9am | 2020 |
| cozmoe | Weightless | | Severe | xyz | img2.png | C | 35 | Piano, Guitar | 1pm-4pm | 2020 |
| cozmoe | Grains of Time | | Moderate | xyz | img3.png | D | 49 | Piano, Guitar | 6pm-12am | 2020 |
| 501A | 501B | | 501D | 501E | 501F | 501G | 501H | 501J | 501K | 501L |

Selects "stressed" and "worried" symptoms

Uses Application Between 18 to 24 (6 pm to 12 am)

User 800

DIGITAL MUSIC THERAPEUTIC SYSTEM WITH AUTOMATED DOSAGE

CROSS-REFERENCE TO RELATED APPLICATIONS

The present application claims priority as a continuation-in-part of U.S. Utility application Ser. No. 17/481,152 for "Digital Music Therapeutic System", filed Sep. 21, 2021, which is incorporated by reference herein in its entirety.

U.S. Utility application Ser. No. 17/481,152 claims priority as a continuation-in-part of U.S. Utility application Ser. No. 16/914,159 for "Restorative Musical Method and System", filed Jun. 26, 2020, which is incorporated by reference herein in its entirety.

U.S. Utility application Ser. No. 16/914,159 claims priority as a continuation-in-part of U.S. Utility application Ser. No. 16/879,580, for "Restorative Musical Method and System", filed May 20, 2020, which is incorporated by reference herein in its entirety.

TECHNICAL FIELD

The present document relates to techniques for automatically identifying, generating, curating, and outputting restorative music.

BACKGROUND

Many workers in the U.S. and in other countries suffer from work-related stress among other stressors throughout their daily lives. It is known that stress contributes to major health problems including cardiovascular and psychiatric disease. Poor sleep, stress, and anxiety are a leading cause of disease in young people and adults.

Some common treatments for poor sleep, stress, and anxiety are meditation and medication, as well as a variety of lifestyle choices such as eating healthy and exercising. However, these solutions can take a significant amount of time, investment, and discipline, and often do not provide instant relief.

Additionally, solutions such as medication may have unwelcome side effects, thus causing more issues. For people who have not mastered meditation, a quiet environment is necessary to receive its stress relieving benefits. Meditation is also something that typically requires training and is not a natural skill most people acquire.

SUMMARY

In various embodiments, the system and method described herein provide functionality for automatically identifying, generating, curating, personalizing, and/or outputting musical compositions and/or other audio programs so as to identify, provide, and/or enhance the effectiveness of such audio programs in addressing the severity of symptoms related to anxiety, insomnia, dementia, and other mental health disorders. Based on a listener's particular inputs via mental health surveys such as GAD-2, GAD-7, DSM and/or other screening tool(s) relating to stress, anxiety, and/or other conditions, the system and method can automatically generate, compose, curate, identify, personalize, and/or play particular audio programs, and can recommend the appropriate listening time to alleviate and/or address such issues related to the listener's level of symptomatology. Additionally, in at least one embodiment, the system can automatically set a duration timer to track the length of time an audio program is played and/or to provide an automated listening experience by, for example, automatically playing the audio program for a specified period of time based on the listener's level of symptomatology.

For example, in at least one embodiment, the system and method can automatically generate or identify an audio program such as a musical composition having a plurality of audio elements, a start and an end, and a slow tempo, so as to mitigate or relieve stress and anxiety in a listener. Audio elements in the musical composition may include, for example, a musical phrase adapted to repeat within the musical composition, an instrumentation including soft tones and pulsating sounds, a plurality of arrangements, and/or a field recording element. Such audio elements may be organized to form a melody. Furthermore, audio mixing the audio elements may allow the musical composition to have moving stereo imaging. The combination of the audio elements of the musical composition can yield neural entrainment, resulting in a calm and relaxed mental state.

In at least one embodiment, metadata describing various audio characteristics of audio programs can be generated and stored, based on analysis of the audio programs. Such metadata can indicate the appropriateness of a particular audio program (or portion thereof) in addressing particular conditions such as trouble sleeping, stress, anxiety, and/or the like. In at least one embodiment, the described system and method can use such metadata to automatically identify, generate, and/or curate musical compositions and/or other audio programs, and to match such programs with particular conditions and issues, so as to maximize effectiveness in addressing such issues in listeners.

In at least one embodiment, the described system and method can personalize music for a particular listener, so as to maximize the effectiveness of the music in reducing symptoms of anxiety and/or stress. Based on input representing the listener's symptoms, AI-assisted algorithms process metadata and generate, identify, and/or play music that is tailored to the needs of that individual listener.

In at least one embodiment, detailed symptomatic metadata is attributed to each audio content item (such as a song), tailoring the music to cater to the severity of symptoms. For example, symptoms can be categorized as mild, moderate, or severe, or any other type of categorization can be used. Metadata is assigned to the audio files based on any number of characteristics, such as: time of day, instruments used, key, tempo, biometrics, and symptoms.

In at least one embodiment, detailed symptomatic metadata is attributed to each audio content item (such as a song), categorizing the music to treat various symptoms such as irritability, trouble sleeping, lack of focus, and the like. Metadata is assigned to the audio files based on any number of characteristics, such as: time of day, instruments used, key, tempo, biometrics, and symptoms.

In at least one embodiment, the system may automatically determine, based on survey responses indicating the severity of the user's symptoms, a dosage (or prescription) for audio programs to be output for the user. The dosage may include a length (or duration) of the musical composition or how long it is played, as well as an indication of how frequently (e.g., how many times per hour/day/week) the musical composition should be played for the user. The dosage may also specify a recommended time of day the user should listen to the audio program. Additionally, the system may periodically check in with the user by prompting the same or similar survey in order to refine the dosage and highlight progress.

In at least one embodiment, visual output may also be provided in connection with the audio program. For example, the system may automatically output waves, nature scenery, breathing guides, and/or the like to help the user further relax.

The system and method thus provide a mechanism for relieving stress and promoting relaxation. In addition, the techniques herein have the added advantage of time-efficiency, since listening to a musical composition or other audio program can generate immediate results.

Further details and variations are described herein.

BRIEF DESCRIPTION OF THE DRAWINGS

The accompanying drawings, together with the description provided below, illustrate several embodiments. One skilled in the art will recognize that the particular embodiments illustrated in the drawings and described herein are merely exemplary, and are not intended to limit scope.

FIG. 3 is a table depicting research study data summarizing electroencephalography (EEG) results of the techniques described herein.

DETAILED DESCRIPTION OF THE EMBODIMENTS

What follows is a description of various aspects, embodiments and/or examples. The aspects, embodiments and/or examples described herein are presented for illustrative purposes, and are not intended to limit the scope of the claims. One skilled in the art will recognize that various structural and/or logical modifications could be made without departing from essential characteristics of the described system and method, as defined by the claims. Therefore, the scope of the claims encompasses their equivalents.

System Architecture

Figure 7:
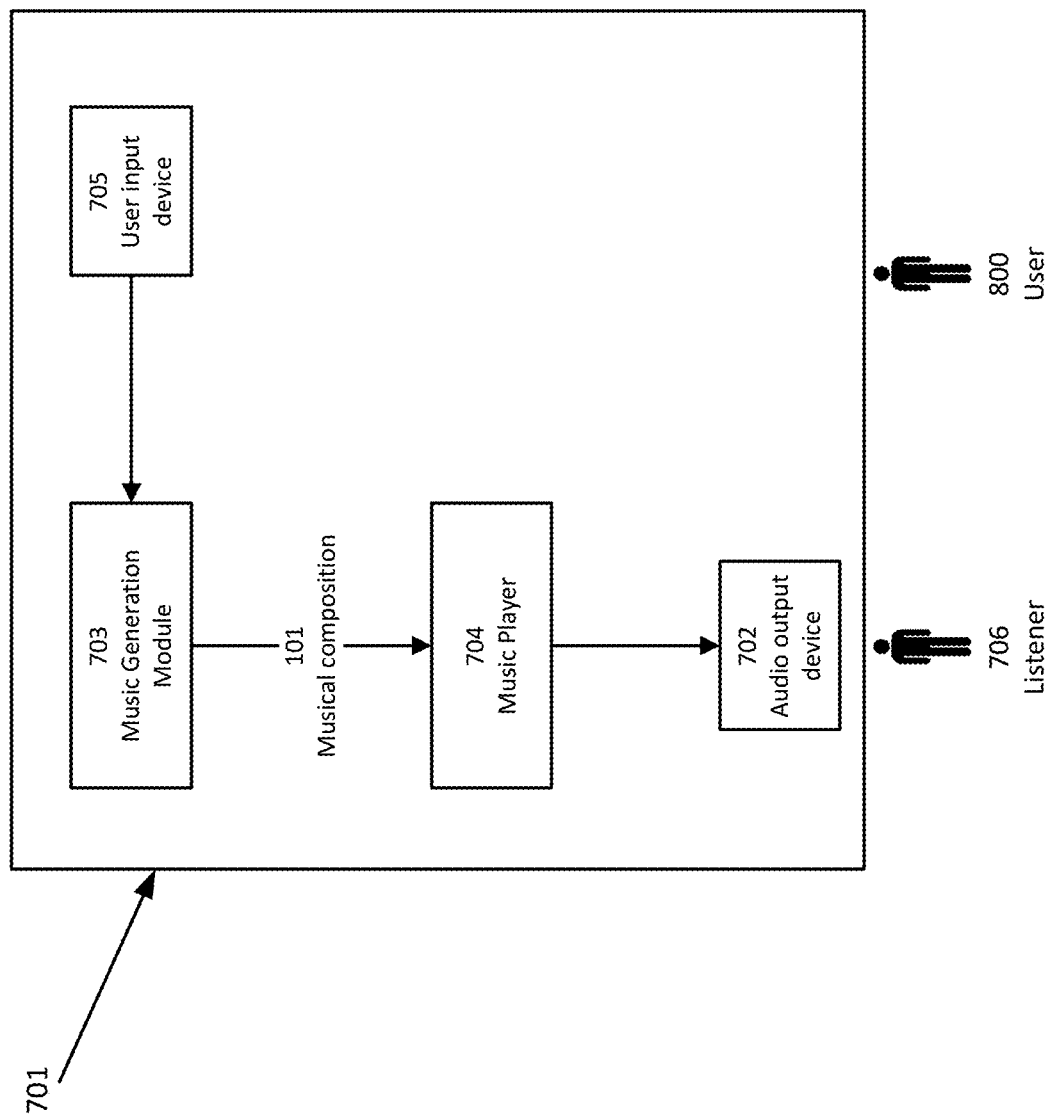
FIG. 7 is a block diagram depicting a system for identifying, generating, curating, and/or playing restorative music according to one embodiment.

Referring now to FIG. 7, there is a shown block diagram depicting a system 701 for identifying, generating, curating, and/or playing restorative music for listener 706 (who may be user 800 or may be another individual) according to one embodiment. The techniques described herein may be performed by music generation module 703, which may be implemented in hardware, software, or any combination thereof, and which is configured to identify and/or generate musical composition 101 according to techniques that are described in more detail below. In at least one embodiment, music generation module 703 may be implemented as software running on a computing device such as a computer, smartphone, tablet, VR/AR headset or the like. In at least one embodiment, music generation module 703 may operate automatically, to identify and/or generate musical composition 101 according to automated techniques described herein and/or according to known techniques. Parameters and settings for identifying and/or generating musical composition 101 may be determined automatically, or may be configured based on input from user 800 (who may be the same individual as listener 706 or may be a different individual), such as may be provided via user input device 705. In various embodiments, user input device 705 may be a keyboard, touchscreen, mouse, microphone, speech recognition module, and/or any other suitable input device.

In at least one embodiment, music generation module 703 may operate under the direction of user 800, so as to manually generate musical composition 101. In yet another embodiment, user 800 can generate musical composition 101 by other means.

Musical composition 101 is sent to music player 704, which may be any known hardware and/or software device for playing music. Music player 704 outputs musical composition 101 via any suitable audio output device 702, such as speaker(s), headphones, a surround sound system, and/or the like. In at least one embodiment, musical composition 101 may be accompanied by visual output, such as may be shown on a display device such as display screen 803 of FIG. 8 or 9. Such visual output can be, for example, a color therapy program that complements musical composition 101. In yet another embodiment, musical composition 101 can be synchronized with visual output presented through a virtual reality (VR) device such as a headset; in such an embodiment, haptic output can also be presented to further engage listener 706 with musical composition 101 and its accompanying output, for a more complete and immersive experience.

In some embodiments, one or more components, as shown and described below in connection with FIGS. 8 and 9, may be used to implement the system and method described herein. Such components may be implemented in a stand-alone electronic device or in a cloud computing-based client/server architecture, using, for example, Amazon Web Services, an on-demand cloud computing platform available from Amazon.com, Inc. of Seattle, Washington. One skilled in the art will recognize that the system and method can be implemented using other architectures.

According to various embodiments, the system and method can be implemented on any electronic device or set of interconnected electronic devices, each equipped to receive, store, retrieve, and/or present information. Each electronic device may be, for example, a server, desktop computer, laptop computer, smartphone, tablet computer, and/or the like. As described herein, some devices used in connection with the system described herein are designated as client devices, which are generally operated by end users. Other devices are designated as servers, which generally conduct back-end operations and communicate with client devices (and/or with other servers) via a communications network such as the Internet. In at least one embodiment, the methods described herein can be implemented in a cloud computing environment using techniques that are known to those of skill in the art. Further details concerning such architectures are provided below in connection with FIGS. 8 and 9.

In addition, one skilled in the art will recognize that the techniques described herein can be implemented in other contexts, and indeed in any suitable device, set of devices, or system. Accordingly, the following description is intended to illustrate various embodiments by way of example, rather than to limit scope.

Figure 8:
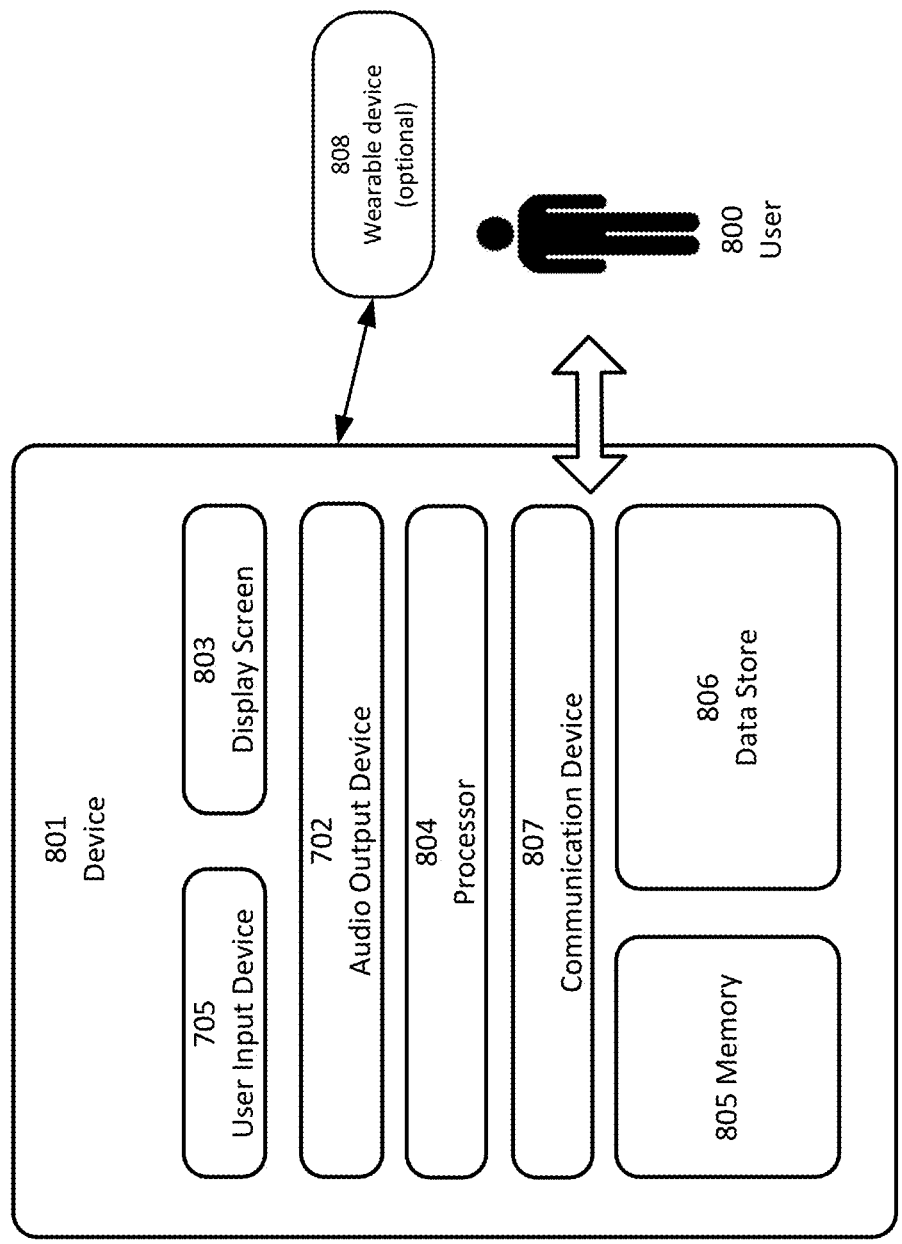
FIG. 8 is a block diagram depicting a hardware architecture for implementing the techniques described herein according to one embodiment.

Referring now to FIG. 8, there is shown a block diagram depicting a hardware architecture for implementing the techniques described herein according to one embodiment. Such an architecture can be used, for example, for implementing the techniques of the system in a computer, smart phone, or other device 801. Device 801 may be any electronic device capable of performing the functions and operations described herein.

In at least one embodiment, device 801 includes a number of hardware components that are well known to those skilled in the art. User input device 705 can be any element that receives input from user 800, including, for example, a keyboard, mouse, stylus, touch-sensitive screen (touch-screen), touchpad, trackball, accelerometer, microphone, speech recognition module, or the like. Input can be provided via any suitable mode or combination of modes, including for example, one or more of: pointing, tapping, typing, dragging, and/or speech. In at least one embodiment, user input device 705 can be omitted or functionally combined with one or more other components. User 800 may be listener 706, or may be a different individual.

Data store 806 can be any magnetic, optical, or electronic storage device for data in digital form; examples include flash memory, magnetic hard drive, CD-ROM, DVD-ROM, or the like. In at least one embodiment, data store 806 stores information that can be utilized, displayed, and/or output according to the techniques described below. Data store 806 may be implemented in a database or using any other suitable arrangement. In another embodiment, data store 806 can be stored elsewhere, and data from data store 806 can be retrieved by device 801 when needed for processing and/or presentation to user 800. Data store 806 may store one or more data sets, which may be used for a variety of purposes and may include a wide variety of files, metadata, and/or other data.

In at least one embodiment, data store 806 may store data such as digital files representing musical compositions, metadata associated with such musical compositions, and/or metadata describing symptoms to be addressed, as well as any other information that may be used in performing the methods described herein. In at least one embodiment, such data can be stored at another location, remote from device 801, and device 801 can access such data over a network, via any suitable communications protocol. In at least one embodiment, multiple data stores 806 may be provided, and information may be divided among such multiple data stores 806 in any suitable manner.

In at least one embodiment, data store 806 may be organized in a file system, using well known storage architectures and data structures, such as relational databases. Examples include Oracle, MySQL, and PostgreSQL. Appropriate indexing can be provided to associate data elements in data store 806 with each other. In at least one embodiment, data store 806 may be implemented using cloud-based storage architectures such as NetApp (available from NetApp, Inc. of Sunnyvale, California), Amazon S3 (available from Amazon, Inc. of Seattle, Washington), and/or Google Drive (available from Google, Inc. of Mountain View, California).

Data store 806 can be local or remote with respect to the other components of device 801. In at least one embodiment, device 801 is configured to retrieve data from a remote data storage device when needed. Such communication between device 801 and other components can take place wirelessly, by Ethernet connection, via a computing network such as the Internet, via a cellular network, or via any other appropriate communication systems.

In at least one embodiment, data store 806 is detachable in the form of a CD-ROM, DVD, flash drive, USB hard drive, or the like. Information can be entered from a source outside of device 801 into a data store 806 that is detachable, and later displayed after the data store 806 is connected to device 801. In another embodiment, data store 806 is fixed within device 801.

In at least one embodiment, data store 806 may be organized into one or more well-ordered data sets, with one or more data entries in each set. Data store 806, however, can have any suitable structure. Accordingly, the particular organization of data store 806 need not resemble the form in which information from data store 806 is displayed or presented to user 800. In at least one embodiment, an identifying label is also stored along with each data entry, to be displayed along with each data entry.

Display screen 803 can be any element that displays information such as text and/or graphical elements. In particular, display screen 803 may display a user interface for prompting user 800 to enter information about symptoms, as well as to allow user 800 to control output of music, set preferences, and/or the like. In at least one embodiment where only some of the desired output is presented at a time, a dynamic control, such as a scrolling mechanism, may be available via user input device 705 to change which information is currently displayed, and/or to alter the manner in which the information is displayed. In at least one embodiment, user input device 705 may be a microphone and/or speech recognition module, allowing user 800 to enter input via speech.

Audio output device 702 may be any suitable device for outputting a musical composition or other audio program. Audio output device 702 may be integrated in device 801, as shown in FIG. 8, or it may be a separate component that communicates with device 801. Audio output device 702 may be, for example, speaker(s), headphones, a surround sound system, and/or the like.

Processor 804 can be a conventional microprocessor for performing operations on data under the direction of software, according to well known techniques. Memory 805 can be random-access memory, having a structure and architecture as are known in the art, for use by processor 804 in the course of running software.

A communication device 807 may communicate with other computing devices through the use of any known wired and/or wireless protocol(s). For example, communication device 807 may be a network interface card ("NIC") capable of Ethernet communications and/or a wireless networking card capable of communicating wirelessly over any of the 802.11 standards. Communication device 807 may be capable of transmitting and/or receiving signals to transfer data and/or initiate various processes within and/or outside device 801.

In at least one embodiment, device 801 is communicatively coupled with wearable device 808, such as a smart watch, virtual reality headset, or other device. In at least one embodiment, wearable device 808 is worn by user 800 (or listener 706), and can monitor symptoms and conditions such as heart rate (pulse), breathing rate, body temperature, perspiration, blood glucose level, heart irregularities such as arrhythmia, and/or the like. As described in detail herein, in at least one embodiment, the described system can use information from wearable device 808 to identify symptoms experienced by user 800 (or listener 706), so as to effectively select, generate, and/or curate music and/or other audio programming to address such symptoms. One skilled in the art will recognize that wearable device 808 is optional.

Figure 9:
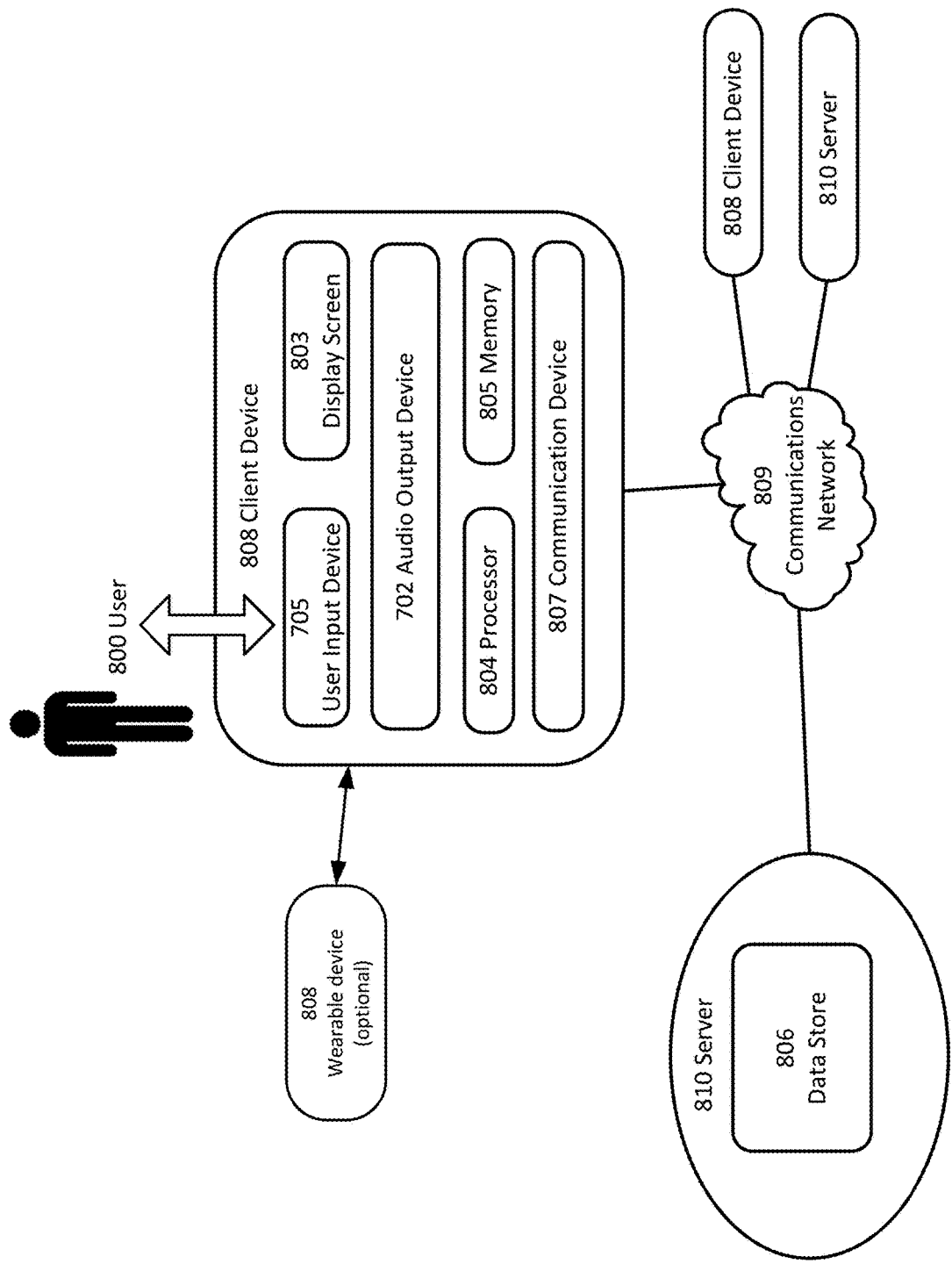
FIG. 9 is a block diagram depicting a hardware architecture for implementing the techniques described herein in a client/server environment, according to one embodiment.

Referring now to FIG. 9, there is shown a block diagram depicting a hardware architecture in a client/server environment, according to one embodiment. Such an implementation may use a "black box" approach, whereby data storage and processing are done completely independently from user input/output. An example of such a client/server environment is a web-based implementation, wherein client device 808 runs a browser that provides a user interface for interacting with web pages and/or other web-based resources from server 810. Items from data store 806 can be presented as part of such web pages and/or other web-based resources, using known protocols and languages such as Hypertext Markup Language (HTML), Java, JavaScript, and the like.

Client device 808 can be any electronic device incorporating user input device 705 and/or display screen 803, such as a desktop computer, laptop computer, personal digital assistant (PDA), cellular telephone, smartphone, music player, handheld computer, tablet computer, kiosk, game system, wearable device, or the like. Any suitable type of communications network 109, such as the Internet, can be used as the mechanism for transmitting data between client device 808 and server 810, according to any suitable protocols and techniques. In addition to the Internet, other examples include cellular telephone networks, EDGE, 3G, 4G, 5G, long term evolution (LTE), Session Initiation Protocol (SIP), Short Message Peer-to-Peer protocol (SMPP), SS7, Wi-Fi, Bluetooth, ZigBee, Hypertext Transfer Protocol (HTTP), Secure Hypertext Transfer Protocol (SHTTP), Transmission Control Protocol/Internet Protocol (TCP/IP), and/or the like, and/or any combination thereof. In at least one embodiment, client device 808 transmits requests for data via communications network 109, and receives responses from server 810 containing the requested data. Such requests may be sent via HTTP as remote procedure calls or the like. As mentioned above, in various embodiments, user input device 705 may be a keyboard, touchscreen, mouse, microphone, speech recognition module, and/or any other suitable input device.

In one implementation, server 810 is responsible for data storage and processing, and incorporates data store 806. Server 810 may include additional components as needed for retrieving data from data store 806 in response to requests from client device 808.

As also set forth in FIG. 8, data store 806 may be organized into one or more well-ordered data sets, with one or more data entries in each set. Data store 806, however, can have any suitable structure, and may store data according to any organization system known in the information storage arts, such as databases and other suitable data storage structures. As in FIG. 8, data store 806 may store data depicting representing musical compositions, metadata associated with such musical compositions, and/or metadata describing symptoms to be addressed, as well as any other information that may be used in performing the methods described herein; alternatively, such data can be stored elsewhere (such as at another server) and retrieved as needed.

In addition to or in the alternative to the foregoing, data may also be stored in a data store 806 present in client device 808. In some embodiments, such data may include elements distributed between server 810 and client device 808 and/or other computing devices in order to facilitate secure and/or effective communication between these computing devices.

As also set forth in FIG. 8, display screen 803 can be any element that displays information such as text and/or graphical elements. Various user interface elements, dynamic controls, and/or the like may be used in connection with display screen 803.

As also set forth in FIG. 8, audio output device 702 may be any suitable device for outputting a musical composition or other audio program. Audio output device 702 may be integrated in device 801, as shown in FIG. 8, or it may be a separate component that communicates with device 801. Audio output device 702 may be, for example, speaker(s), headphones, a surround sound system, and/or the like.

As also set forth in FIG. 8, processor 804 can be a conventional microprocessor for use in an electronic device to perform operations on data under the direction of software, according to well known techniques. Memory 805 can be random-access memory, having a structure and architecture as are known in the art, for use by processor 804 in the course of running software. A communication device 807 may communicate with other computing devices through the use of any known wired and/or wireless protocol(s), as also set forth in the description of FIG. 8.

Notably, multiple servers 810 and/or multiple client devices 808 may be networked together, and each may have a structure similar to those of client device 808 and server 810 that are illustrated in FIG. 9. The data structures and/or computing instructions used in the performance of methods described herein may be distributed among any number of client devices 808 and/or servers 810. As used herein, "system" may refer to any of the components, or any collection of components, from FIG. 8 and/or 9, and may include additional components not specifically described in connection with FIGS. 8 and 9.

In some embodiments, data within data store 806 may be distributed among multiple physical servers. Thus, data store 806 may represent one or more physical storage locations, which may communicate with each other via the communications network and/or one or more other networks (not shown). In addition, server 810 as depicted in FIG. 9 may represent one or more physical servers, which may communicate with each other via communications network 109 and/or one or more other networks (not shown).

In one embodiment, some or all components of the system can be implemented in software written in any suitable computer programming language, whether in a standalone or client/server architecture. Alternatively, some or all components may be implemented and/or embedded in hardware.

In at least one embodiment, music generation module 703 as shown in FIG. 7 can be implemented on device 801 shown in FIG. 8 or FIG. 9, or any other electronic device having input, output, processing, and memory components as is known in the art.

Furthermore, the functions and/or method steps set forth below may be carried out by software running on one or more of device 801, client device(s) 808, server 810, and/or other components. This software may optionally be multi-function software that is used to retrieve, store, manipulate, and/or otherwise use data stored in data storage devices such as data store 806, and/or to carry out one or more other functions.

Musical Composition 101

Figure 1:
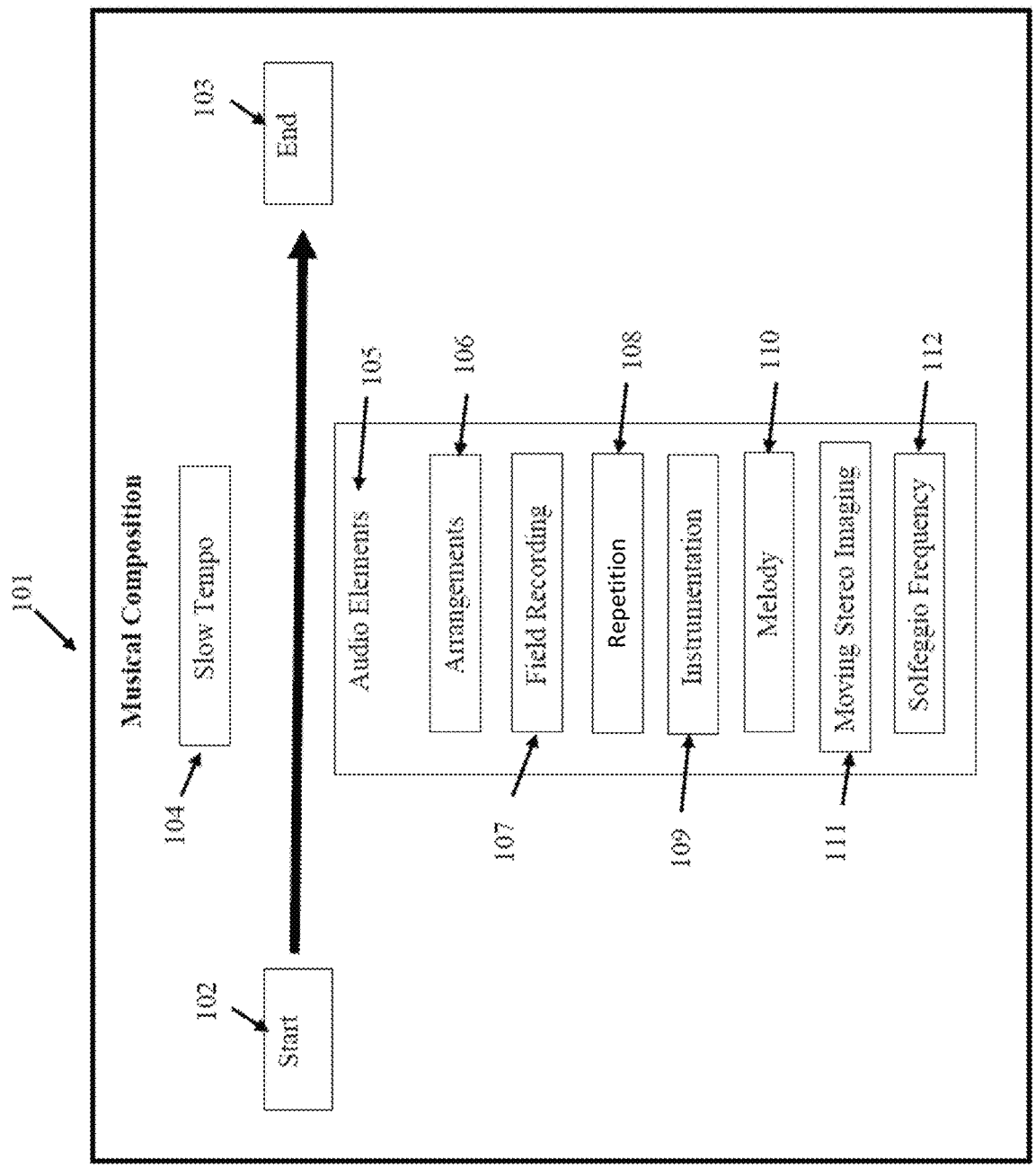
FIG. 1 depicts an example of a musical composition, as may be composed, curated, and/or played according to one embodiment.

Referring now to FIG. 1, there is shown an example of a musical composition 101, as may be identified, generated, analyzed, composed, curated, and/or played according to one embodiment. In at least one embodiment, musical composition 101 may be a professional sound recording having start 102 and end 103, which may incorporate a variety of compositional and mixing techniques that, when played by music player 704 and output via audio output device 702, may yield meditative benefits for listener 706. Such musical composition 101 allows listener 706 to relax, thus reducing listener's 706 stress levels.

In at least one embodiment, musical composition 101 may contain a combination of musical elements ("audio elements 105"). Such elements 105 may include, for example, repetition 108, plurality of arrangements 106 which may be successional and form a gradual build, instrumentation 109, field recording(s) 107, melody(ies) 110, moving stereo imaging 111, and/or solfeggio frequency(ies) 112. In addition, musical composition 101 may have a slow tempo 104, and may incorporate pulsating sounds (or isochronic tones). Each of these will be described in turn.

In particular, the combination of various elements 105 as depicted in FIG. 1 may work together to promote relaxation in the human body and decrease side effects of high stress levels. As a result, musical composition 101, when listened to by listener 706, can effectively reduce stress in listener 706 by virtue of the combination of particular audio elements 105 and/or other factors. In at least one embodiment, musical composition 101 may further allow listener 706 to have better focus once in his or her relaxed state.

Any suitable mixing techniques may be used, including, for example, 3D imaging and/or equalization (EQ) of solfeggio frequencies 112. In at least one embodiment, musical composition 101 is restorative in nature and may therefore be used as a method of treatment for stress, as will be described herein.

Repetition 108

In at least one embodiment, musical composition 101 incorporates repetition 108. For example, musical composition 101 may include a phrase ("musical phrase"), such as, for example, a chord progression and/or a melody that is repeated any number of times. The use of repetition 108 can result in brainwave entrainment, also referred to as neural entrainment, in which the aggregate frequency of oscillations produced by the synchronous electrical activity in ensembles of cortical neurons can adjust to synchronize with the periodic vibration of an external stimuli, such as a sustained acoustic frequency (perceived as pitch), or a regularly repeating pattern of intermittent sounds (perceived as rhythm). Particular patterns of neural firing may correspond with states of alertness such as focused attention and deep sleep.

Repetition 108 helps facilitate shifts in brainwave state by using entrainment. A repeating musical phrase, such as a melody or chord progression, can be used from start 102 to end 103 of musical composition 101, providing a stable frequency to which the brainwave can attune. By using repetitive rhythm and frequency, entrainment can occur; this makes it possible to down-shift listener's 706 normal beta state (normal waking consciousness) to alpha (relaxed consciousness).

Slow Tempo 104

In at least one embodiment, musical composition 101 may have a slow tempo 104. The tempo of a song refers to the speed at which a piece of music is or should be played. It is known that a song's tempo can influence listener's 706 heart rate. In at least one embodiment, musical composition 101 plays at a slower pace to reflect a resting heart rate. For example, musical composition 101 may have a tempo range of between 40 and 65 beats per minute to reflect the slower heart rate. A higher heart rate typically indicates a stressed or active state; thus, the slow tempo encourages a slowing heart rate and reduces stress. The slow tempo in combination with the other elements of the musical composition further facilitates relaxation for listener 706.

Arrangements 106

In at least one embodiment, musical composition 101 may have arrangements 106 that are added in progression to draw listener 706 into the composition. The addition of each arrangement 106 in a progression draws listener 706 in by introducing individual audio elements in succession. In other words, not all of the audio elements of musical composition 101 necessarily begin at the same time; for example, a repeating phrase may be introduced, followed by a gradual buildup of audio elements, thus creating a more relaxing listening environment. In another example, audio elements may be introduced simultaneously in a way that does not disturb or distract listener 706, such as by introducing each audio element at a different volume level, using a gradual succession wherein the volume level of each audio element is balanced in different ways. For example, the arrangement may begin with a repeating phrase upon which musical composition 101 can be built.

Introducing each arrangement in succession also does not interfere with listener's 706 focus on the anchor but creates a more enjoyable listening environment. Beginning musical composition 101 with the phrase arrangement allows listener 706 to be drawn in slowly, thus keeping listener 706 engaged on the musical composition. Having listener 706 engaged while listening to the entire composition further allows listener 706 to focus on relaxing throughout the entire musical composition 101.

Soft Tones

In at least one embodiment, musical composition 101 has an instrumentation that uses soft tones. A soft tone refers to sound sources which tend to have longer attack and/or release times and quieter transients. This helps soften the envelope's characteristics, resulting in a subjectively more pleasant and less abrasive tone.

Pulsating Sounds

In at least one embodiment, musical composition 101 may also have an instrumentation that uses pulsating sounds. For example, the instrumentation may utilize synthesizers, percussion, guitar, and/or other musical elements including synthetic and natural instruments and sounds. The pulsating sound is defined by repeatedly increasing and decreasing volume level of a soft tone, to resemble a pulse. In at least one embodiment, the pulsating sound is subliminally or evidently used in musical composition 101 to achieve stress-reducing benefits and/or improve focus.

Melody 110

In at least one embodiment, the plurality of audio elements 105 in musical composition 101 may be disposed to form a melody 110. Melody 110 allows musical composition 101 to be distinguishable from other pieces of music by making it more memorable to listener 706. Melodies are pleasing sequences of musical notes, which may increase listener 706 enjoyment of the composition. In at least one embodiment, melody 110 is used in musical composition 101 to engage listener 706 in a pleasing and novel activity rather than only providing a form of stress relieving treatment. Melody 110 may also increase commercial appeal because it is musically satisfying, and may help ensure that musical composition 101 is pleasant and unique-sounding to listener 706 while still including stress-relieving elements.

In at least one embodiment, a dosage may also be specified, including a length and frequency. Length (or duration) may be the length of musical composition 101 or how long it is played. Frequency may be an indication of how frequently (e.g., how many times per hour/day/week) musical composition 101 should be played for the user. In at least one embodiment, dosage, including length and frequency, may be automatically determined based on input such as questionnaire responses or the like, as described herein.

In at least one embodiment, during playback of musical composition 101, a duration timer may be automatically started, to keep track of the length of time that the user has been listening to musical composition 101. Once the specified length of time has elapsed, playback of musical composition 101 may automatically stop. In at least one embodiment, a gradual fadeout may be applied, so as to avoid a sudden stoppage of playback that may be jarring.

In at least one embodiment, the system may track completed sessions, which include sessions in which the user has listened to musical composition 101 for the time period as specified in the determined dosage. The system may also track the total number of minutes that the user has listened to musical composition(s) 101 provided by the system. Such metrics, and/or others, may be used as a basis for gamification milestones, which may encourage the user to complete the treatment plan through a points system. For example, points collected by various users can be used to encourage healthy competition among users, track rankings based on comparisons among users, provide rewards and perks, and/or the like.

In at least one embodiment, another timer may be used, referred to as a "reminder timer", based on the determined frequency with which musical composition 101 should be played for the user. Playback may automatically begin at specified intervals, based on the reminder timer. Alternatively, when the reminder timer indicates that it is time for playback to begin, an automated reminder may be output, to remind the user to begin playback at the next convenient opportunity.

Moving Stereo Imaging 111

In at least one embodiment, the plurality of audio elements 105 may be adapted to cause or evoke moving stereo imaging 111. Stereo imaging is the perceived spatial location of the sound source, both laterally and in depth, with each sound and/or instrument in musical composition 101 being configured to appear to play from a specific location in the sound field. Moving stereo imaging 111 allows audio elements to have apparent movement and to fluidly flow from different apparent sound sources. Moving stereo imaging 111 allows the individual audio elements, sounds, and/or instruments of the musical composition to create a combined multidimensional (3D) experience for listener 706, in which various sonic elements move in a way that stimulates different hemispheres of the brain. For example, moving stereo imaging 111 may produce a Doppler effect, in which both the frequency and volume of a sound (or combination of sounds) change as a sound source travels across the stereo field. Moving stereo imaging 111 may also include custom phase-oscillated movements, multi-binaural stereo, and/or comb filtering to create different perceived depth of each audio element. Moving stereo imaging 111 further allows audio elements 105 to sound as if each audio element 105 is moving through the stereo field.

In addition, moving stereo imaging 111 allows listener 706 to have a dynamic sound experience, which may help stimulate and focus listener's 706 brain while engaging with musical composition 101. Moving stereo imaging 111 may allow the sounds of musical composition 101 to slowly move from one sound source to another, such as from one speaker to another speaker. In another example, musical composition 101 may play from one ear to the other while listener 706 is using headphones.

Solfeggio Frequency 112

In at least one embodiment, musical composition 101 includes audio elements that emphasize one or more solfeggio frequencies 112. Solfeggio frequencies 112 are specific tones of sound that may help promote various aspects of body and mind health. In at least one embodiment, audio elements 105 of musical composition 101 are mixed so as to amplify the resonance of one or more solfeggio frequencies 112, thereby emphasizing such frequencies. For example, audio elements 105 of musical composition 101 may be mixed to play at a range of 500 Hz to 600 Hz, which is a common solfeggio frequency range. In another example, solfeggio frequencies 112 may be boosted by applying equalization (EQ) to various audio elements 105 of musical composition 101. Equalization is performed by adjusting the frequency of audio elements 105 in composition 101 based on their frequency. In at least one embodiment, the plurality of audio elements 105 may be audio mixed to play at a solfeggio frequency 112. In another embodiment, a separate tone at a particular frequency (such as 40 Hz, for example) may be added to promote gamma and theta brain wave oscillations.

Field Recording(s) 107

In at least one embodiment, musical composition 101 includes one or more field recordings 107. Field recordings 107 are audio recordings produced outside a recording studio, and may include both natural and human-made sounds. Field recordings 107 may soften musical composition 101, so as to make it seem more natural or organic, and less synthetic. Some examples of field recording elements 107 include sounds of the ocean, birds, a running stream or river, rustling leaves, and/or gentle breathing. The addition of one or more field recordings 107 may further make musical composition 101 more enjoyable for listener 706. Field recordings 107 also provide a natural element to further help listener 706 relax. In particular, nature sounds can help reduce stress.

Instrumentation 109

Instrumentation 109 of musical composition 101 may have soft tones and may also have a pulsating sound. In at least one embodiment, instrumentation 109 may be adapted be introduced in succession. In at least one embodiment, instrumentation 109 may be adapted to repeat from start 102 to end 103 of musical composition 101.

Output Via Music Player 704

In at least one embodiment, musical composition 101 may be adapted to be played by music player 704 and be audible through audio output device 702. The combination of each audio element 105 in the restorative musical composition may allow listener 706 to experience the benefits of stress relief that may be designed to increase alpha brain wave activity. The elements work cohesively to create a listening environment that promotes relaxation. It is known that once someone is more relaxed, they can focus more effectively. In at least one embodiment, the system may automatically determine a dosage (specified, for example, as a length/duration of listening and a frequency of listening such as a certain number of times per day or week), which may be prescribed based on received input representing responses to a mental health survey or questionnaire. By automatically playing musical composition 101 for a specified length of time, and repeating playback according to the specified frequency of listening, the described system enables a passive experience for the listener requiring little to no manual operation by the listener.

Visual Output

In at least one embodiment, visual output may also be provided in connection with the audio program. For example, the system may automatically output waves, nature scenery, breathing guides, and/or the like to help the user further relax.

Method

Figure 4:
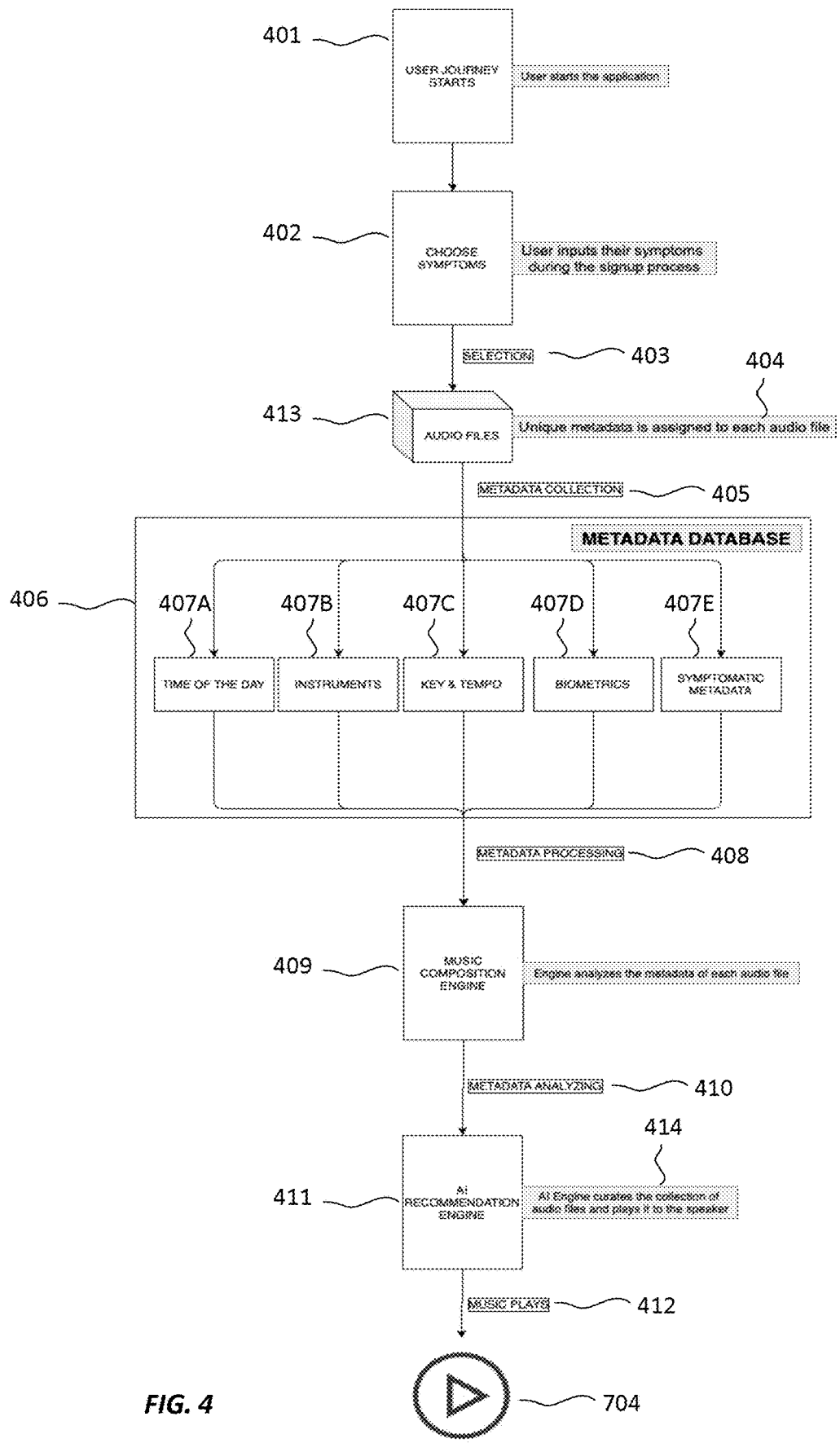
FIG. 4 is a flow diagram depicting a method for implementing the techniques described herein according to one embodiment.

Referring now to FIG. 4, there is shown a flow diagram depicting a method for implementing the techniques described herein according to one embodiment. In at least one embodiment, the steps depicted in FIG. 4 may be performed by a computing device such as device 801 shown in FIG. 8 or FIG. 9, or by any other electronic device having input, output, processing, and memory components as is known in the art. In at least one embodiment, the computing device may include music generation module 703 as shown in FIG. 7, and user 800 may provide input via user input device 705. Musical output is sent from music player 704 for output at audio output device 702. One skilled in the art will recognize, however, that the steps depicted in FIG. 4 may be performed using any suitable architecture, which may be different from those depicted in FIG. 7, 8, or 9.

In at least one embodiment, music generation module 703 (or another connected component) includes an artificial intelligence (AI) engine that is capable of interpreting input describing the severity of listener's 706 symptoms, and generating and/or curating music in a manner that can address the severity of those symptoms. For example, such an engine may be implemented as software running on processor 804 of device 801 or client device 808. Accordingly, many of the steps depicted in FIG. 4 can be performed by an AI engine running on a computing system such as device 801 or client device 808.

In a first step 401, user 800 (who may be listener 706 or another user) starts the application. In at least one embodiment, step 401 may include creating an account, inputting user information via a mental health screening tool, and/or the like. In response, the system triggers an event that starts accepting metadata to be used in identifying, generating, and/or curating music for listener 706, and automatically playing music for the recommended amount of time.

In step 402, which may be performed as part of a setup process, user 800 identifies the symptoms to be addressed by the system. Any suitable user input mechanism can be used, such as for example user input device 705. In at least one embodiment, the system can prompt user 800 with a list of questions shown on display screen 803, to better understand the severity of symptoms, and user 800 selects from the list. Alternatively, user 800 can simply enter symptoms via a keyboard, or can speak about the severity of the symptoms (for example, by saying, "I'm constantly feeling tired"). User's 800 selection 403 can then be used to personalize the audio experience for listener 706 (who, again, may be the same individual as user 800 or may be a different individual). In at least one embodiment, the system can also identify symptoms automatically, by monitoring user 800 (and/or listener 706) behavior, or by receiving signals from wearable device 808, or performing other actions.

In at least one embodiment, the system includes a backend that collects user metadata in response to user entry of degree/severity of symptoms. Such metadata can include, for example, user ID, user country and time zone, selected symptoms and/or their severity (mild, moderate, severe), device information, subscription info, tapping events, engagement ratios, intent score, and/or the like. The collected user metadata is then stored in an electronic storage device such as data store 806. In at least one embodiment, this user data may be referred to collectively as a particular "AI bucket". As described in more detail below, the user metadata can be matched against audio file metadata so as to generate recommendations for creating and/or curation of music and other audio programming.

In step 404, metadata is assigned to each of a number of different audio files 413. In at least one embodiment, user 800 is presented with a loading screen while step 404 takes place. Audio files 413, along with their associated metadata, may be stored in data store 806 or any other suitable data storage device.

Metadata 405 is stored in metadata database 406, which may be stored in data store 806 or any other suitable data storage device.

In at least one embodiment, two different types of metadata can be provided: A primary bucket can store metadata associated with audio files 413, so as to specify instruments 407A, symptoms 407E that may be addressed by each audio file, key & tempo 407C, and the like. A secondary bucket can store metadata associated with listeners 706, such as a unique listener ID, severity of symptoms experienced 407E, time of day 407A, biometrics 407D, and/or the like. Both buckets of metadata can be stored in metadata database 406, which may itself be stored in a single data store 806, or in separate data stores 806, or in distributed storage as is known in the art. In at least one embodiment, the system can employ cloud-based storage for any or all of the data to be stored.

In at least one embodiment, the AI of the described system uses three different variable types to implement a weighted matrix factorization technique that is used to match metadata and thereby select an effective audio program to address the particular level/severity of symptoms experienced by the listener 706, as follows:

Dynamic variables: these can change over the course of the user journey. For example, predefined user-based filtering IDs may be modified once user 800 changes the metadata representing listener 706 symptoms. Examples of dynamic variables include artist id, track id, symptoms id, album id, metadata id, timeofday id, instruments id, tempo id, key id, and/or the like.

Static variables: these represent core data used by the matching algorithm. The AI uses these variables when mapping structured data representing music metadata with specific needs of listener 706. Examples of static variables include symptom level/severity id, user id, and/or the like.

Temporary variables: these may be used by processor 804 on a temporary basis when running algorithms and performing processing. Normally, such variables are discarded rather than being stored permanently in data store 806.

In at least one embodiment, the AI of the described system learns latent factor representations for users 800 as well as for items in the audio file dataset. In this manner, the AI is able to perform automated matching between music programs and specific needs of listener 706.

Processed information from user 800 and audio files may be stored in data store 806, for example in a relational database 406 such as PostgreSQL or the like; such an arrangement provides for ease of training and validation of a machine learning model for implementing the techniques described herein.

Once metadata stored in database 406 has been processed 408, it is provided by music composition engine 409, which in one embodiment may be a component of music generation module 703. Music composition engine 409 analyzes metadata of each audio file from database 406. Results 410 of this analysis are passed to AI recommendation engine 411, which in one embodiment may be a component of music generation module 703. In at least one embodiment, AI recommendation engine 411 curates 414 the collection of available audio files to generate recommendations for listener 706. Based on these recommendations, suitable musical compositions and/or other audio programs are provided to music player 704 for output via audio output device 702. In at least one embodiment, AI recommendation engine 411 uses any of a number of different clustering algorithms to pair the best-matching audio program with each particular listener 706, and to specify a length/duration for playing the audio program. In at least one embodiment, the system may automatically end the music and stop playback when the suggested listening length/duration has expired. Automatic fadeout may be used so as not to cause a jarring discontinuity when the music stops.

In at least one embodiment, AI recommendation engine 411 applies content-based and collaborative filtering on the analyzed audio files, and can also curate based on similar users' behavior and preferences. For example, the AI recommendation engine 411 can use metadata collected from other users with similar interactions and/or inputs, and can select audio files that such other users have played the most or have indicated they like the most. The result of the curation step 414 is that a unique score matrix can be applied to each audio file or track.

In at least one embodiment, to further personalize listener's 706 experience, a user interface may be presented, for example via a "Personalize" section of an app or website, to prompt listener 706 regarding the symptom(s) and/or condition(s) he or she is experiencing. Such prompts may include, for example, question prompts in accordance with recognized surveys or questionnaires to identify anxiety and/or other disorders and conditions. One example of such a survey is the Generalized Anxiety Disorder 2 (GAD-2) survey; however, other surveys, prompts, questionnaire, and/or questions can be used. In at least one embodiment, such prompts may be presented again on a periodic basis, or when listener 706 attains certain listening milestones or thresholds, so as to update listener's 706 condition In at least one embodiment, the system can develop a score based on listener's 706 responses to such a survey or questionnaire, wherein the score represents listener's 706 level of anxiety. Appropriate musical composition(s) and/or other audio content can then be selected, curated, and/or customized based on the developed score.

In at least one embodiment, such customization may include automatically shortening or lengthening the duration of playback of the musical composition(s) to match a specified duration that is determined based on an assessment of listener 706. Such shortening or lengthening may be performed, for example, by automatically truncating the musical composition(s) (i.e., stopping playback before the musical composition(s) has ended), or automatically repeating playback of the musical composition(s) in a loop until the specified length/duration has been reached.

In at least one embodiment, such customization may include automatically playing the musical composition(s) a certain number of times per hour, day, or week, according to a specified frequency of playback that is determined based on an assessment of listener 706.

Once AI recommendation engine 411 has curated 414 the collection of audio files, the music is ready to be played. In at least one embodiment, a "play music" button is displayed on screen 803. When user 800 clicks on the button, the music plays 412 on music player 704.

In at least one embodiment, the system is voice-activated, so that, rather than clicking on a "play music" button, user 800 can initiate playback of restorative music by speaking a voice command.

Voice Input to Identify Symptoms

In at least one embodiment, the system interprets user 800 speech not only to initiate playback of restorative music, but also to identify symptoms to be addressed by the restorative music, and assess the severity of such symptoms. For example, user 800 (who may or may not be listener 706) may speak a phrase such as, "I'm extremely tired" or "I'm a little bit nervous" or "I'm totally stressed out" into an audio input device such as a microphone associated with a smartphone, smart watch, or other electronic device. Alternatively, user 800 may be given the opportunity to respond to survey questions via spoken input. The system interprets the spoken input using known natural language processing techniques, and assesses the severity of symptoms associated with the spoken input. When generating, selecting, and/or curating musical composition(s) 101 for playback, the system can take into account the identified symptom(s), for example by generating, identifying, selecting, and/or curating musical composition(s) 101 that have metadata that indicates that such musical composition(s) 101 are effective at addressing the identified symptom(s) and recommending an appropriate dosage, including a listening time per session and number of listening times (sessions) per day. In this manner, the system provides users 800 with an easy-to-use mechanism for initiating playback of restorative music that can address listener's 760 symptoms, by speaking a short phrase or sentence identifying such symptoms and their severity, and/or by responding to survey questions.

For example, in one embodiment, user 800 opens an app on his or her smartphone, or initiates a software application on any other device. User 800 is prompted with a question such as "Over the past two weeks, have you felt nervous, anxious, or on edge?" User 800 may respond by typing or speaking an explanation of how he or she feels. For example, "More than half the days." Based on this input, the system automatically generates, selects, and/or curates musical composition(s) 101 for playback, for example by matching metadata associated with musical composition(s) 101 with the identified symptoms, and plays music tailored to help listener's 760 symptoms, including automatically playing the music for a specific amount of time and a certain number of times per day or week. In the example, the system can select and play musical composition(s) 101 having metadata tags representing severity of symptoms such as "severe" and "moderate".

Figure 5:
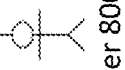
FIG. 5 is a table depicting examples of metadata that can be associated with an audio program, according to one embodiment.

Referring now to FIG. 5, there is shown a table 500 depicting examples of metadata that can be associated with an audio program, according to one embodiment. Columns 501A through 501L represent different types of metadata for different musical selections, including for example: artist name 501A, track name 501B, symptom severity 501D that the musical selection can address, album 501E, album artwork filename 501F, key 501G, tempo 501H (in beats per minute), instruments 501J, suitable time of day 501K for playback of the musical selection, and year 501L.

In the example of FIG. 5, user 800 specifies that the music is to be played from 6 pm to 12 midnight. In response, AI recommendation engine 411 matches these values with the appropriate audio file metadata to curate the output to include audio programs that will satisfy the specified criteria. In at least one embodiment, the appropriate dosage for the audio program may be automatically configured to be output for user 800 within the specified hours.

One skilled in the art will recognize that other mechanisms can be used to identify symptoms of listener 706 to be addressed. For example, user 800 can type input, select from on-screen prompts, provide speech input, or provide input in any other suitable way.

In at least one embodiment, the system can be coupled to a device that can measure physical characteristics, symptoms, or conditions of listener 706 (such as pulse (heart rate), blood pressure, breathing rate, arrhythmia, exertion level, and/or the like) and interpret such characteristics to determine what symptoms listener 706 may be experiencing. Such a device may be wearable device 808, such as a smart watch. The system can thereby detect symptoms automatically without requiring explicit input from user 800 or listener 706. In yet another embodiment, the system can access health records of listener 706, so as to determine what symptoms listener 706 may be experiencing; for example, if listener 706 has a history of depression, the system can play music to address depression.

AI Training and Validation Method

Figure 6:
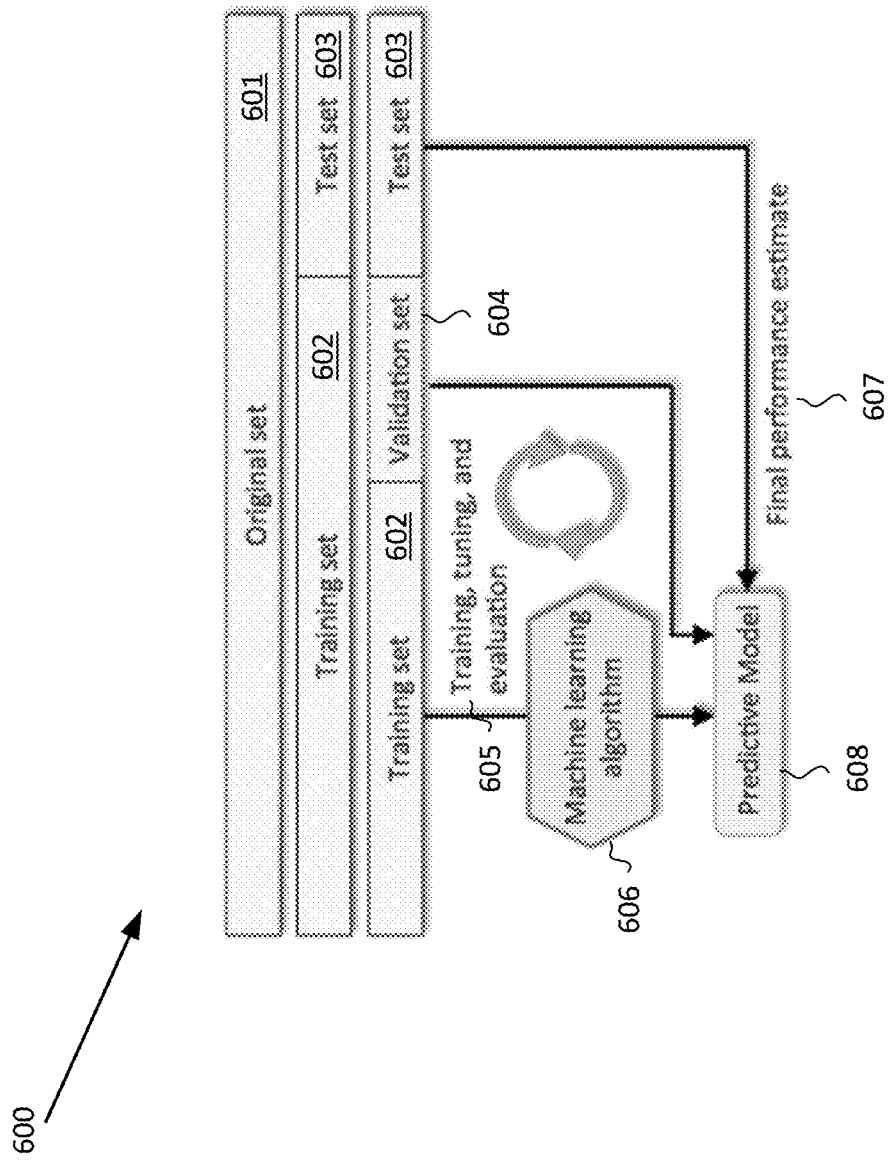
FIG. 6 is a block diagram depicting a method for iterative training and validation of a machine language algorithm to develop a predictive model for curation of audio programs, according to one embodiment.

Referring now to FIG. 6, there is shown a block diagram depicting a method 600 for iterative training and validation of a machine language algorithm, as may be used by AI recommendation engine 411 to develop a predictive model 608 for curation of audio programs such as musical compositions, according to one embodiment.

In at least one embodiment, for training and validation, original data 601 is split into training data set 602, validation set 604, and test data set 603. Training data set 602 is used by machine learning algorithm 606 in an iterative process 605 of training, tuning, and evaluation of predictive model 608. Various algorithms, techniques, and functions are run on training data set 602, and a determination is made as to whether the expected output is generated expected outputs. In at least one embodiment, training data set 602 contains sample data including audio files and user's 800 behavioral inputs.

In at least one embodiment, training data set 602 includes two buckets of data:
Primary Bucket: contains metadata of 50 audio files (sample)
Secondary Bucket: contains metadata of 50 users (sample).

Such buckets of information can be obtained, for example from a database stored in data store 806. The buckets are processed using batch analysis in order to receive feedback as to the quality of predictive model 608.

In at least one embodiment, some of the original data 601 is split off into a validation data set 604. Feedback is validated over training data set 602 to provide an unbiased evaluation of the fitness of model 608. If the expected output is not accurate, model 608 re-evaluates its accuracy, and various hyperparameters can be automatically or manually tuned. Such hyperparameters may include any parameters that model 608 does not learn by itself but that are provided to model 608 before it starts learning. Examples of such hyperparameters include the number of hidden units in a neural network, the number of trees in a Random Forest, the K number of nearest neighbors in a K-nearest neighbor (KNN) algorithm, and the like. In at least one embodiment, the system is able to facilitate experimentation with various available strategically approved scenarios to improve the accuracy of the algorithm.

Test data set 603 is used to test the fitness of predictive model 608, and to refine model 608. For example, predictive model 608 can be tested using the audio files dataset, which may include metadata that is embedded granularly within each audio file. Examples of such metadata include timeof-day id, instruments id, symptoms id, track id, artist id, tempo id, key id, year id, album id, year id, and the like. In at least one embodiment, predictive model 608 can be tested without any metadata to see whether it performs adequately and provides accurate or expected recommendations. If not, then predictive model 608 is reevaluated using training data set 602. This process of training, tuning, and evaluation 605 is performed iteratively until final performance estimate 607 indicates that predictive model 608 is sufficiently fit.

Assigning Symptoms Through Song Structure

In at least one embodiment, each piece of music is assigned unique metadata that is used by AI recommendation engine 411 in the curation process 414, wherein such metadata is matched to the needs and preferences of listener 706. Symptomatic metadata 407E is defined by how each individual piece of music yields a desired effect. The desired effect may be achieved, for example, by applying variations in compositional techniques, playback techniques, or the like.

As an example, a song associated with sleep may be generated/composed using a slower tempo (for example, 40 beats per minute), gentle instrumental velocity (for example, using soft synthesizers), and a gradual build in the arrangement over time. By contrast, a piece of music designed to energize listener 706 might have a faster tempo (for example, 65 beats per minute), louder instrumental velocity, and a more pronounced build in the arrangement. Metadata associated with such a song would identify these characteristics, so that AI recommendation engine 411 can curate audio programs and play appropriate music based on the particular needs and preferences of listener 706.

Composing Using Artificial Intelligence

In at least one embodiment, the restorative music generated by the described system can be composed via artificial intelligence. A collection of audio files with individual solo performances featuring guitar, piano, synthesizer, field recordings and the like can be employed. These files are composed and delivered by musicians, and stored in data store 806. Using the techniques described herein, an artificial intelligence composition engine has access to the database of audio files and rearranges them using unique metadata associated with each individual audio program, which helps the artificial intelligence composition engine understand how to prioritize composing, arranging, and mixing components.

EEG Study

Restorative music system 701 described herein can be used for treatment for stress. As mentioned, stress is a growing problem for personal health. Restorative music system 701 may generate music that can help listener 706 reduce his or her stress level and further improve his or her everyday health and well-being, since stress can cause a multitude of other health problems. Furthermore, this method of treatment may be used at any time, such as when working or engaging in sporting activities or the like.

An electroencephalogram (EEG) study was conducted to evaluate the benefits of the method and system described herein. The study was conducted at the Nielsen Consumer Neuroscience San Francisco location and consisted of sixty-four participants (50% male and 50% female) between the ages of 21 and 34. The experiment's group of 32 participants listened to ten minutes of restorative musical compositions generated by a system 701 similar to that described herein, while an equivalent control group of 32 participants went through the same protocol, except that they listened to ten minutes of music that was not designed to reduce stress.

The results of the study concluded that music from restorative music system 701 led to a 23-percent reduction in reported stress levels. The results of the study also concluded that, compared to the control group, restorative music system 701 also succeeded in having a restorative effect on the participants' brain state. During the ten minutes of the restorative musical composition, the experimental group participants showed a 13-percent increase in EEG markers of memory activation, specifically increases in theta and gamma band brain oscillations. This data was gathered to see if the music also stimulates the memory cortex of the brain. Memory activation can be defined as the formation of connections with new and past experiences in the amygdala. Additionally, as the experimental group participants listened to the restorative musical composition, they exhibited greater attentional focus as indexed by a decrease in alpha band EEG activity. After the experimental group participants stopped listening to the restorative musical composition, the experimental group participants showed an overall decrease in attention processing, measured by increases in alpha activity. The results of the study showed an overall decrease in attention processing which yielded a calming effect on the listeners.

Figure 2:
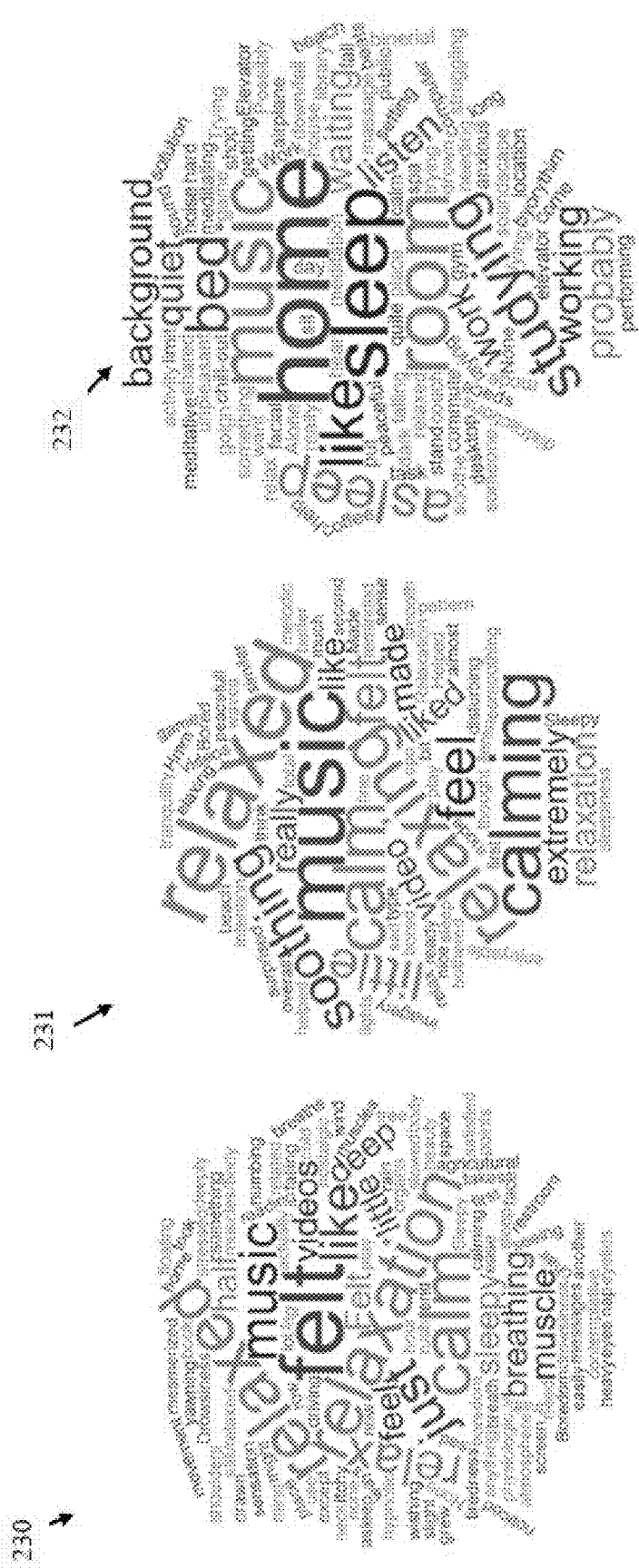
FIG. 2 depicts an example of a graphic of a participant's responses to a research study's questions, according to one embodiment.

The participants were asked to respond to the following open-ended questions after listening to the musical composition: what physiological sensations did you experience while listening, what's your initial reaction after listening to the music, and in what environment do you see yourself listening to this music. Referring now to FIG. 2, there is shown an example of a graphic of a participant's responses to a research study's questions, according to one embodiment. Element 230 depicts the physiological sensations participants reported, including "relaxation", "calm", and the like. Element 231 depicts participants' initial reaction 231, which also includes similar words such as "relaxed", "calming", and "relaxing". Element 232 depicts environments in which the participants saw themselves listening to the musical composition most, including for example, home, in bed, and while studying.

Attentional processes have been extensively linked to meditation and stress relief in previous research studies. Moreover, lower levels of attention, as indexed by higher alpha band EEG activity, are known to reflect states of calm and relaxation. The results of the described study suggest that restorative music system 701 described herein provides both a memorable and meditative effect on listener 706, resulting in more focused attention during the experience, followed by greater relaxation.

Referring now to FIG. 3, there is shown table 301 depicting research study data summarizing electroencephalography (EEG) results of the techniques described herein. Table 301 reflects the averaged EEG data for both an experimental group and a control group, collected before and after a 10-minute listening session using the system described herein. The findings of the research study are reported on a 10-point scale based on the EEG results. Columns 302A, 302B show participants' scores prior to listening to their assigned music, while columns 302C, 302D show participants' scores after listening to their assigned music for 10 minutes. As shown in table 301, the system described herein leads to lower attention and higher memory, implying a relaxing and memorable experience. As shown, columns 302B, 302D indicate that the experimental group experienced an increase of memory activation of 0.3 (from 5.7 to 6.0) and a decrease of attention processing of 0.4 (from 6.6 to 6.2). Conversely, columns 302A, 302C indicate that the control group had a decrease of memory activation of 0.4 (from 5.7 to 5.3) and an increase of attention processing of 0.9 (from 6.2 to 7.1) after listening to musical composition 101.

Selecting Parameters for Audio Program

Figure 10:
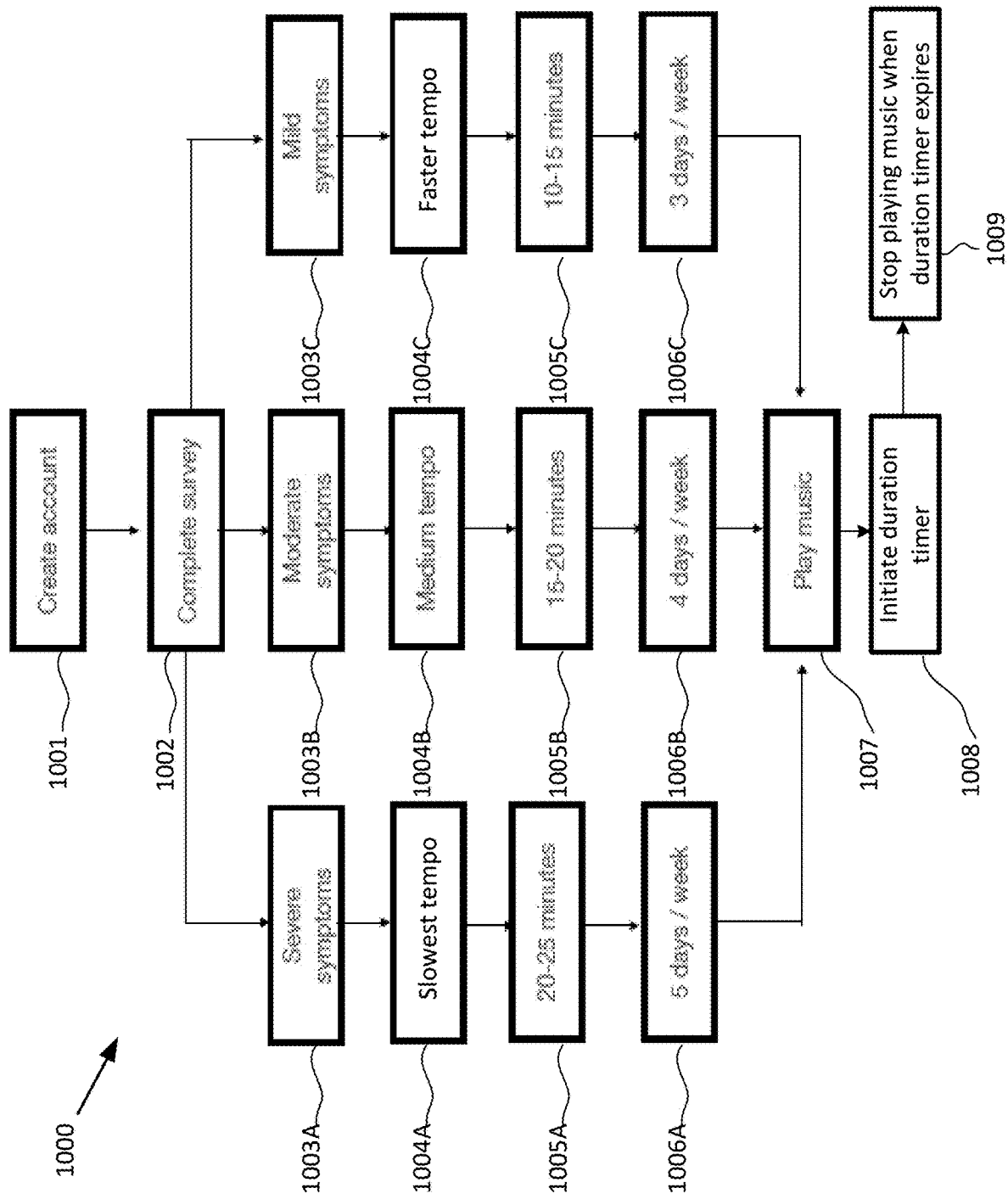
FIG. 10 is a block diagram depicting a method for selecting various parameters for an audio program based on an assessment of symptoms, according to one embodiment.

Referring now to FIG. 10, there is shown a block diagram depicting a method 1000 for selecting various parameters for an audio program based on an assessment of symptoms, according to one embodiment.

The user may create an account 1001, and may complete a survey 1002 indicating the severity of their symptoms. Based on the user's input, a score may be assigned indicating whether the user is experiencing severe symptoms 1003A, moderate symptoms 1003B, or mild symptoms 1003C. Based on this score, the system may assign music with different tempos; for example, a slowest tempo 1004A may be assigned in response to severe symptoms, a medium tempo 1004B may be assigned in response to moderate symptoms, and a faster tempo 1004C may be assigned in response to mild symptoms. In addition, a duration 1005A, 1005B, or 1005C and gratification milestone 1006A, 1006B, or 1006C may be assigned based on the score. Duration 1005A, 1005B, or 1005C may indicate how long the user should listen to the music program, or how long the music program should be played for the user. Frequency 1006A, 1006B, or 1006C may indicate a prescribed or suggested frequency for the user to listen to the music program; the system may suggest playback of a music program at the prescribed frequency, or it may automatically output the music program according to the prescribed frequency. Alternatively, frequency 1006A, 1006B, or 1006C may indicate a gamification threshold or milestone; once the user has listened to the music program at the specified frequency, they may obtain a benefit such as a credit, prize, or other reward.

Once the parameters have been assigned, the music or other audio program may be played 1007 for the user, in accordance with the specified parameters.

In at least one embodiment, a duration timer may be automatically initiated 1008 when the music or other audio program starts playing. The duration timer may be configured to expire after some period of time corresponding to specified duration 1005A, 1005B, or 1005C. When the duration timer expires, the system may automatically stop playing the music or other audio program 1009. In at least one embodiment, a gradual fadeout may be applied, so as to avoid a sudden stoppage of playback that may be jarring.

Definitions

It may be advantageous to set forth definitions of certain words and phrases used in this document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this document, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this document, "and/or" means that the listed items are alternatives, but the alternatives also include any combination of the listed items.

For purposes of the description herein, a "user", such as user 800 referenced herein, is an individual, enterprise, or other group, which may optionally include one or more users. A "data store", such as data store 806 referenced herein, is any device capable of digital data storage, including any known hardware for nonvolatile and/or volatile data storage. A collection of data stores 806 may form a "data storage system" that can be accessed by multiple users. A "computing device", such as device 801 and/or client device(s) 808, is any device capable of digital data processing. A "server", such as server 810, is a computing device that provides data storage, either via a local data store, or via connection to a remote data store. A "client device", such as client device 808, is an electronic device that communicates with a server, provides output to user 800, and accepts input from user 800.

The terms "musical composition", "audio program", "musical program", "track", and "song" may be used interchangeably herein to refer to any audio item that can be generating, identified, curated, and/or composed according to the techniques described herein, and that can be output via speakers, headphones, or some other audio output device. Such audio item may be musical in nature, and/or it may include non-musical elements such as natural sounds. Such audio item may or may not be accompanied by a visual element.

Throughout this document, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements, and features discussed only in connection with one aspect, embodiment, or example are not intended to be excluded from a similar role(s) in other aspects, embodiments, or examples.

Aspects, embodiments, or examples may be described as processes, which may be depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the claims.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the claims. Therefore, the scope of this application is intended to cover such alternate aspects, embodiments and/or examples. Hence, scope is defined by the accompanying claims and their equivalents. Further, each and every claim is incorporated as further disclosure into the specification.

Screen Shots

Figure 11:
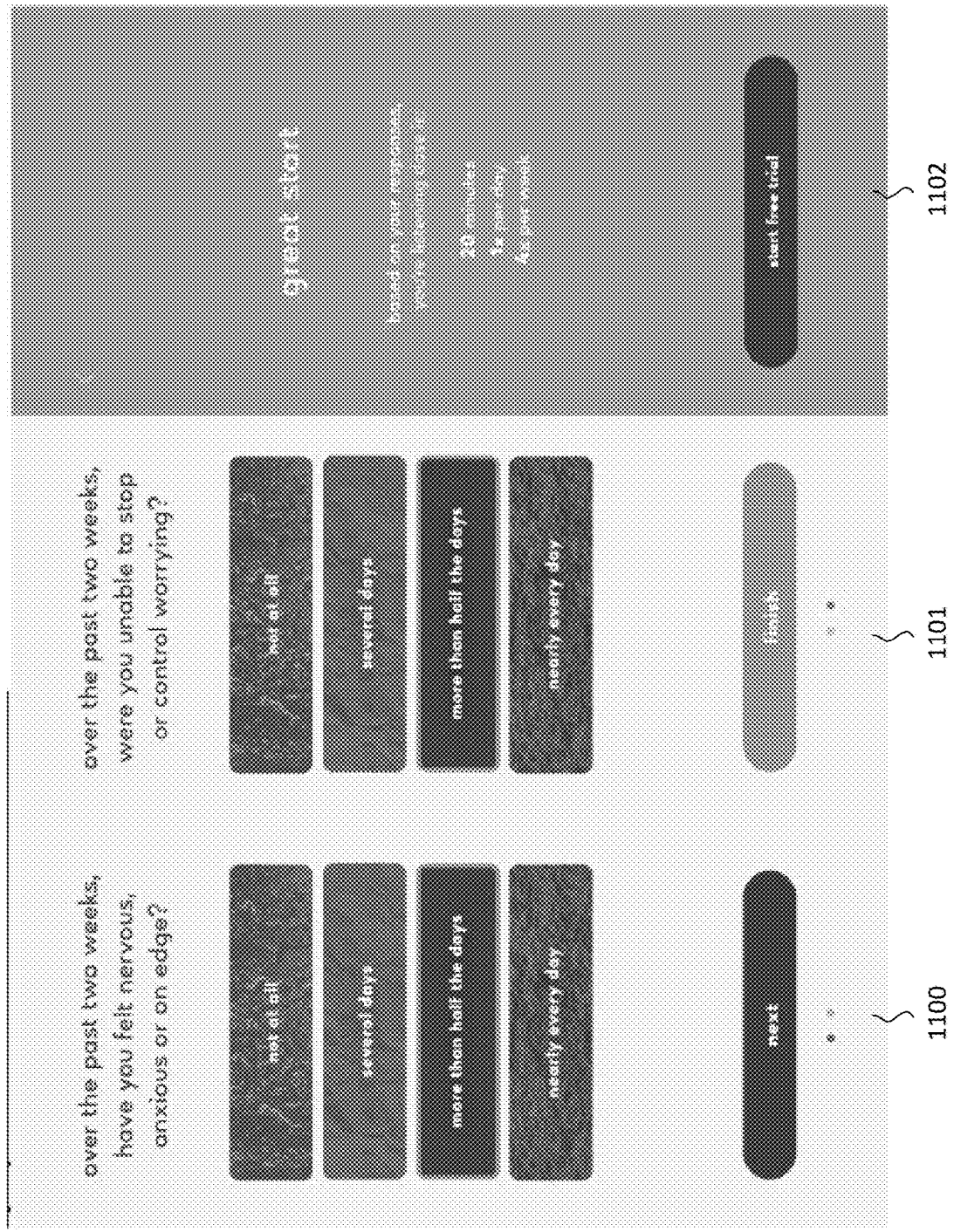
FIG. 11 depicts examples of screenshots for presenting an initial anxiety screening survey, according to one embodiment.

Referring now to FIG. 11, there are shown examples of screenshots 1100, 1101, 1102 for presenting an initial anxiety screening survey for determining whether mild, moderate, or severe symptom treatment is recommended, according to one embodiment. Such screenshots 1100, 1101, 1102 may be presented, for example, after the user registers for the service. The survey score determines whether mild, moderate, or severe symptom treatment is recommended.

Screen 1100 prompts the user to indicate the degree to which they feel nervous, anxious, or on edge. Screen 1101 prompts the user to indicate how frequently they are unable to stop or control worrying. Screen 1102 indicates a listening dosage derived based on the user's responses, and invites the user to commence a free trial of the audio program service.

Figure 12A:
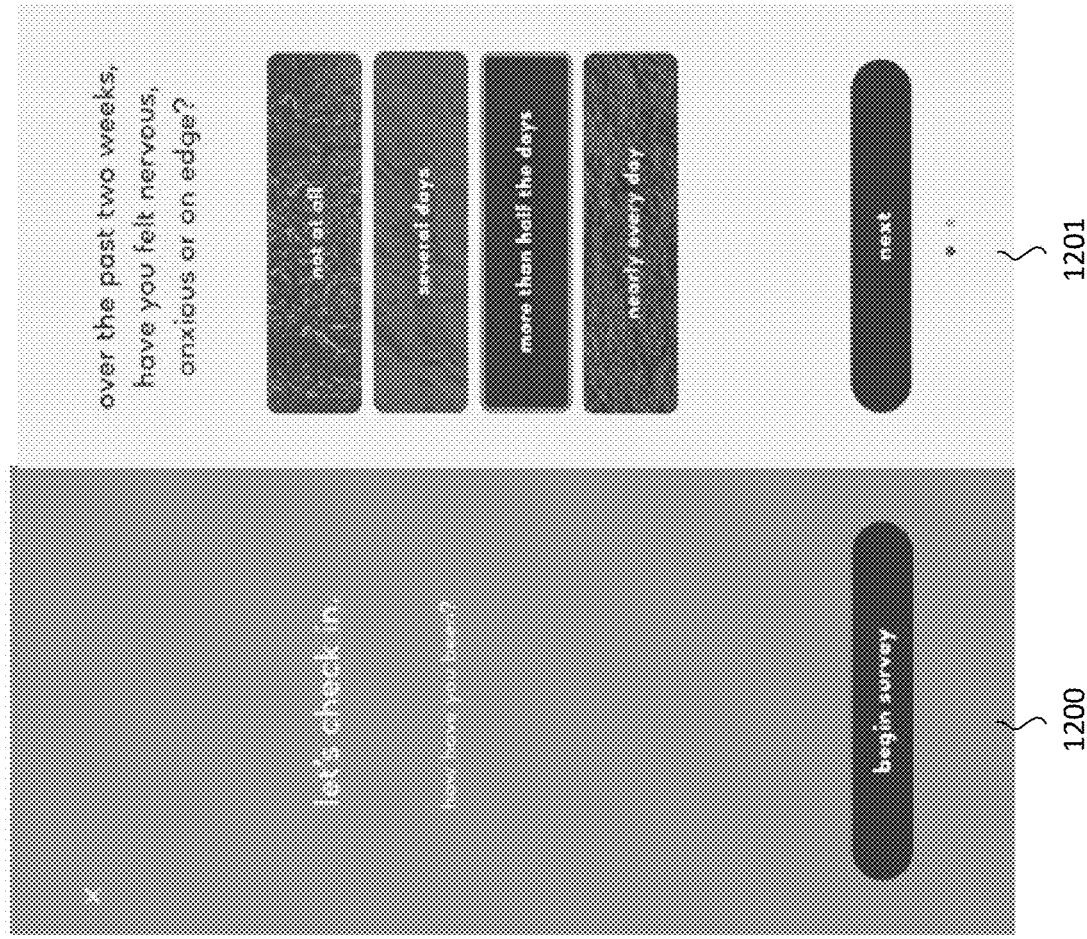
FIGS. 12A and 12B depict examples of screenshots for presenting a supplemental anxiety screening survey, according to one embodiment.
Figure 12B:
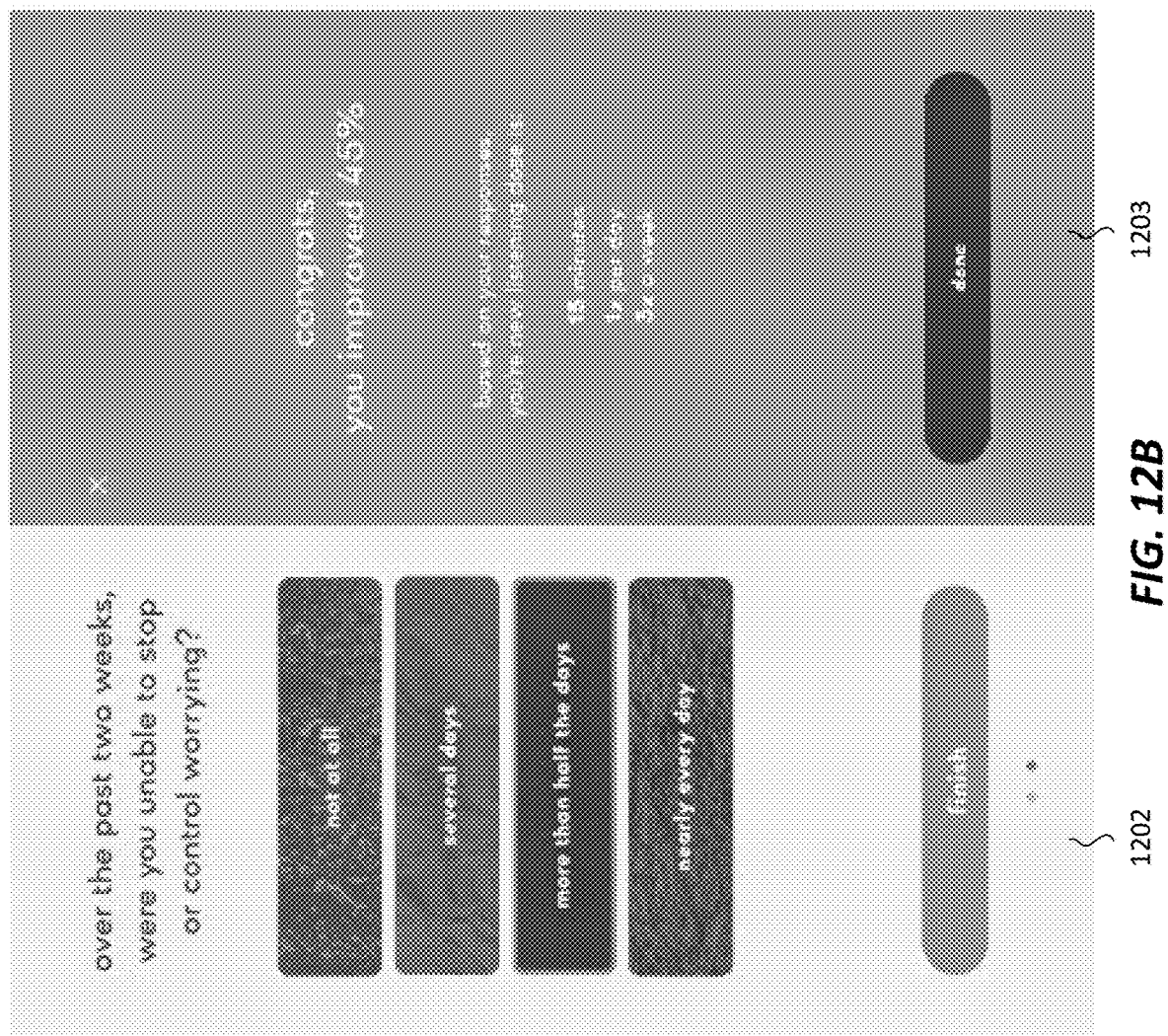

Referring now to FIGS. 12A and 12B, there are shown examples of screenshots 1200 through 1203 for presenting a supplemental anxiety screening survey, according to one embodiment. Such screenshots may be depicted, for example, after the user has used the audio program service for a period of time, such as for example 30 days, and provides an opportunity to update the dosage recommendation.

Screen 1200 prompts the user to begin a survey. Screen 1201 prompts the user to indicate the degree to which they feel nervous, anxious, or on edge. Screen 1202 prompts the user to indicate how frequently they are unable to stop or control worrying. Screen 1203 indicates an updated listening dosage derived based on the user's responses, that better suits the severity of the user's symptoms.

Figure 13:
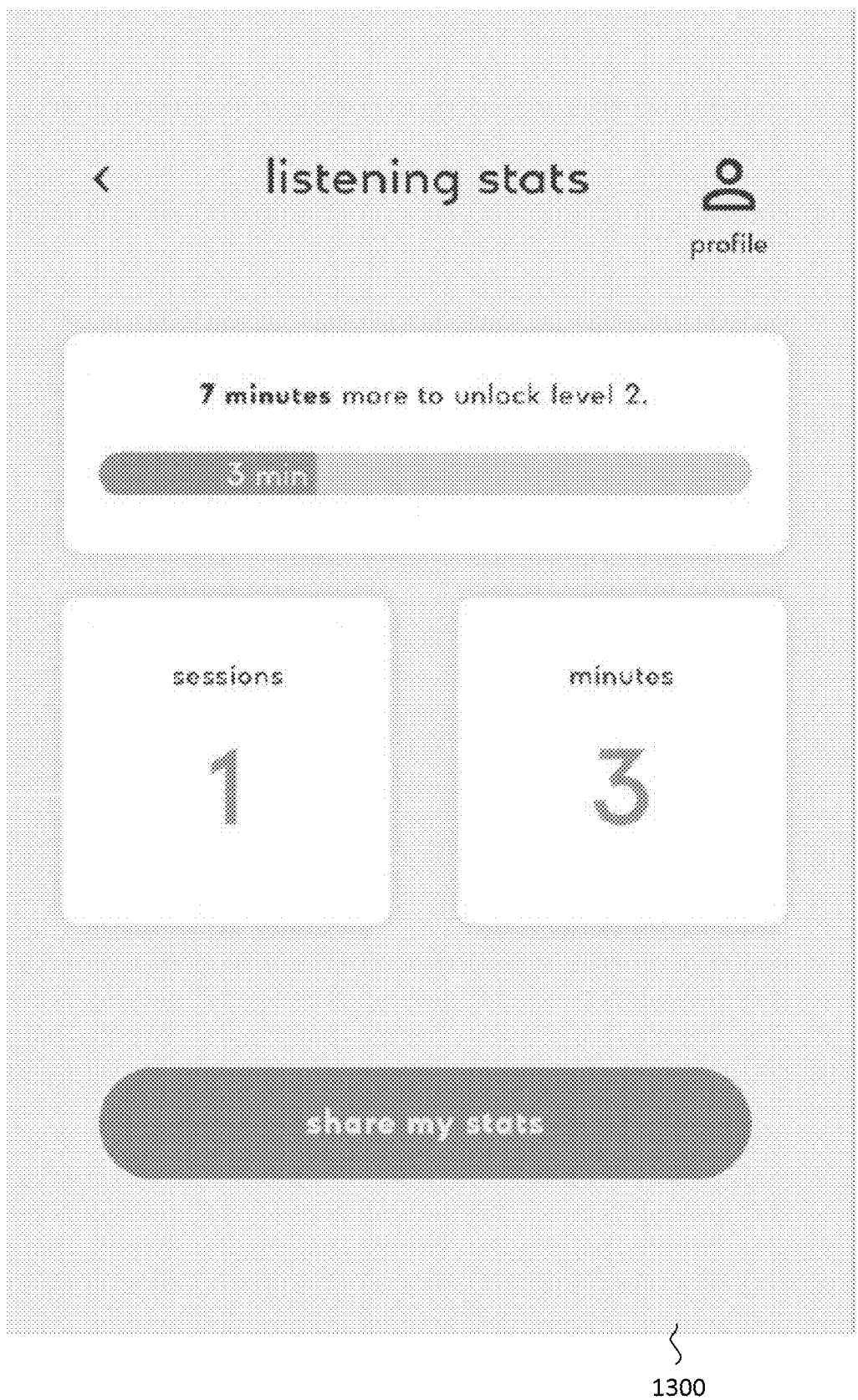
FIG. 13 depicts an example of a screenshot for gamification, according to one embodiment.

Referring now to FIG. 13, there is shown an example of a screenshot 1300 for gamification, according to one embodiment.

In addition to prescribing music and recommending a dosage based on the user's severity of symptoms, the user may be encouraged to complete treatment via gamification techniques within the app, product, or hardware device. For example, the user may be prompted to complete at least a portion of the recommended dosage in order to reach a new level, or to get access to perks and benefits that may be offered via the system or separately. In at least one embodiment, gamification milestones may be determined based on the severity of the user's symptoms.

One skilled in the art will recognize that the screenshots depicted in FIGS. 11 through 13 are merely exemplary, and that other layouts, arrangements, and elements may be provided.

The present system and method have been described in particular detail with respect to possible embodiments. Those of skill in the art will appreciate that the system and method may be practiced in other embodiments. First, the particular naming of the components, capitalization of terms, the attributes, data structures, or any other programming or structural aspect is not mandatory or significant, and the mechanisms and/or features may have different names, formats, or protocols. Further, the system may be implemented via a combination of hardware and software, or entirely in hardware elements, or entirely in software elements. Also, the particular division of functionality between the various system components described herein is merely exemplary, and not mandatory; functions performed by a single system component may instead be performed by multiple components, and functions performed by multiple components may instead be performed by a single component.

Reference in the specification to "one embodiment" or to "an embodiment" means that a particular feature, structure, or characteristic described in connection with the embodiments is included in at least one embodiment. The appearances of the phrases "in one embodiment" or "in at least one embodiment" in various places in the specification are not necessarily all referring to the same embodiment.

Various embodiments may include any number of systems and/or methods for performing the above-described techniques, either singly or in any combination. Another embodiment includes a computer program product comprising a non-transitory computer-readable storage medium and computer program code, encoded on the medium, for causing a processor in a computing device or other electronic device to perform the above-described techniques.

Some portions of the above are presented in terms of algorithms and symbolic representations of operations on data bits within a memory of a computing device. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "displaying" or "determining" or the like, refer to the action and processes of a computer system, or similar electronic computing module and/or device, that manipulates and transforms data represented as physical (electronic) quantities within the computer system memories or registers or other such information storage, transmission or display devices.

Certain aspects include process steps and instructions described herein in the form of an algorithm. It should be noted that the process steps and instructions can be embodied in software, firmware and/or hardware, and when embodied in software, can be downloaded to reside on and be operated from different platforms used by a variety of operating systems.

The present document also relates to an apparatus for performing the operations herein. This apparatus may be specially constructed for the required purposes, or it may comprise a general-purpose computing device selectively activated or reconfigured by a computer program stored in the computing device. Such a computer program may be stored in a computer readable storage medium, such as, but is not limited to, any type of disk including floppy disks, optical disks, CD-ROMs, DVD-ROMs, magnetic-optical disks, read-only memories (ROMs), random access memories (RAMs), EPROMs, EEPROMs, flash memory, solid state drives, magnetic or optical cards, application specific integrated circuits (ASICs), or any type of media suitable for storing electronic instructions, and each coupled to a computer system bus. Further, the computing devices referred to herein may include a single processor or may be architectures employing multiple processor designs for increased computing capability.

The algorithms and displays presented herein are not inherently related to any particular computing device, virtualized system, or other apparatus. Various general-purpose systems may also be used with programs in accordance with the teachings herein, or it may prove convenient to construct more specialized apparatus to perform the required method steps. The required structure for a variety of these systems will be apparent from the description provided herein. In addition, the system and method are not described with reference to any particular programming language. It will be appreciated that a variety of programming languages may be used to implement the teachings described herein, and any references above to specific languages are provided for disclosure of enablement and best mode.

Accordingly, various embodiments include software, hardware, and/or other elements for controlling a computer system, computing device, or other electronic device, or any combination or plurality thereof. Such an electronic device can include, for example, a processor, an input device (such as a keyboard, mouse, touchpad, track pad, joystick, trackball, microphone, and/or any combination thereof), an output device (such as a screen, speaker, and/or the like), memory, long-term storage (such as magnetic storage, optical storage, and/or the like), and/or network connectivity, according to techniques that are well known in the art. Such an electronic device may be portable or non-portable. Examples of electronic devices that may be used for implementing the described system and method include: a mobile phone, personal digital assistant, smartphone, kiosk, server computer, enterprise computing device, desktop computer, laptop computer, tablet computer, consumer electronic device, or the like. An electronic device may use any operating system such as, for example and without limitation: Linux; Microsoft Windows, available from Microsoft Corporation of Redmond, Washington; MacOS, available from Apple Inc. of Cupertino, California; iOS, available from Apple Inc. of Cupertino, California; Android, available from Google, Inc. of Mountain View, California; and/or any other operating system that is adapted for use on the device.

While a limited number of embodiments have been described herein, those skilled in the art, having benefit of the above description, will appreciate that other embodiments may be devised. In addition, it should be noted that the language used in the specification has been principally selected for readability and instructional purposes, and may not have been selected to delineate or circumscribe the subject matter. Accordingly, the disclosure is intended to be illustrative, but not limiting, of scope.

What is claimed is:

1. A system for automatically generating restorative music to mitigate anxiety-related symptoms experienced by a listener, comprising:
    a hardware processor, adapted to, for each of a plurality of audio programs, automatically assign metadata indicating severity of at least one anxiety-related symptom the audio program is able to mitigate;
    an electronic storage device, communicatively coupled to the hardware processor, adapted to store the metadata;
    an output device, communicatively coupled to the hardware processor, adapted to output a survey comprising a plurality of prompts for identifying at least one anxiety-related symptom being experienced by the listener, and for assessing severity of each identified symptom;
    a user input device, communicatively coupled to the hardware processor, adapted to receive input in response to the prompts of the survey, so as to automatically identify at least one anxiety-related symptom being experienced by the listener, and to automatically assess severity for each identified symptom;
    an audio output device, communicatively coupled to the hardware processor, adapted to automatically output at least one of the audio programs to mitigate severity of at least one identified anxiety-related symptom; and
    a duration timer, communicatively coupled to the hardware processor;
    wherein the hardware processor is further adapted to:
    automatically select at least one of the audio programs for output by the audio output device, based on a match between severity of at least one anxiety-related symptom identified in the received input and severity of at least one anxiety-related symptom indicated in the stored metadata for the at least one audio program;
    automatically determine, based on severity of at least one identified symptom, a listening dosage comprising a duration specifying how long to output each selected audio program, and a frequency specifying how many times to output each selected audio program within a period of time; and
    automatically configure each selected audio program to include, within the audio program, a degree of periodic repetition of at least one musical attribute selected from the group consisting of a musical phrase, a chord progression, and a melody, to address the at least one anxiety-related symptom identified in the received input;
    and wherein automatically outputting at least one of the audio programs comprises:
    automatically commencing output of the audio program based on the frequency specified by the listening dosage;
    automatically initiating the duration timer based on the duration specified by the listening dosage; and
    upon expiration of the duration timer, automatically stopping output of the audio program, so as to limit the listener's exposure to the audio program to the duration specified by the listening dosage.

2. The system of claim 1, wherein each of the audio programs comprises a musical composition.

3. The system of claim 2, wherein each musical composition comprises a plurality of audio elements, comprising at least one selected from the group consisting of:
    a phrase that repeats throughout the musical composition;
    a plurality of arrangements, each introduced in succession;
    an instrumentation of soft tones introduced in succession; and
    a field recording element.

4. The system of claim 2, wherein each musical composition comprises at least one selected from the group consisting of:
    a plurality of audio elements disposed to form a melody;
    a plurality of audio elements that are mixed to emphasize solfeggio frequencies;
    a plurality of audio elements adapted to cause moving stereo imaging; and
    a tempo between 40 and 65 beats per minute.

5. The system of claim 2, wherein:
    automatically selecting at least one of the audio programs for output by the audio output device comprises:
        comparing severity of anxiety-related symptoms indicated in the metadata assigned to the audio programs with severity of at least one anxiety-related symptom identified in the received input; and
        selecting at least one musical composition having assigned metadata indicating severity of at least one anxiety-related symptom identified in the received input; and
    automatically outputting the at least one audio program comprises automatically outputting the selected at least one musical composition.

6. The system of claim 2, wherein:
    automatically selecting at least one of the audio programs for output by the audio output device comprises automatically generating at least one musical composition adapted to mitigate severity of at least one anxiety-related symptom identified in the input; and
    automatically outputting the at least one audio program comprises automatically outputting the generated at least one musical composition.

7. The system of claim 1, wherein:
- the user input device comprises an audio input device, adapted to receive spoken input indicating severity of at least one anxiety-related symptom being experienced by the listener; and
- the hardware processor is further adapted to interpret the received spoken input to determine severity of the identified at least one anxiety-related symptom.

8. The system of claim 1, wherein:
- the user input device comprises a device further adapted to automatically detect at least one physical indicator of severity of at least one anxiety-related symptom being experienced by the listener.

9. The system of claim 1, wherein:
- the user input device is further adapted to receive a signal from a wearable device indicating severity of at least one anxiety-related symptom being experienced by the listener.

10. The system of claim 1, wherein the hardware processor is further adapted to automatically determine a score based on the input received in response to the prompts of the survey, and to automatically assess severity of at least one anxiety-related symptom being experienced by the listener based on the determined score.

11. The system of claim 1, further comprising:
- a reminder timer;
- wherein:
- automatically outputting at least one of the audio programs further comprises automatically initiating the reminder timer based on the specified frequency; and
- automatically commencing output of the audio program based on the frequency specified by the listening dosage comprises automatically commencing output of the audio program upon expiration of the reminder timer, so as to output the audio program according to the specified frequency.

12. The system of claim 1, further comprising:
- a visual output device, configured to automatically output a visual relaxation program concurrently with the audio program.

13. A computer-implemented method for automatically generating restorative music to mitigate symptoms experienced by a listener, comprising:
- at a hardware processor, for each of a plurality of audio programs, automatically assigning metadata indicating severity of at least one anxiety-related symptom the audio program is able to mitigate;
- storing the metadata at an electronic storage device;
- at an output device, outputting a survey comprising a plurality of prompts for identifying at least one anxiety-related symptom being experienced by the listener, and for assessing severity of each identified symptom;
- at a user input device, receiving input in response to the prompts of the survey;
- at the hardware processor, based on the received input, automatically identifying at least one anxiety-related symptom being experienced by the listener, and automatically assessing severity of each identified symptom;
- at the hardware processor, automatically selecting at least one of the audio programs, based on a match between severity of at least one anxiety-related symptom identified in the received input and severity of at least one anxiety-related symptom indicated in the stored metadata for the at least one audio program;
- at the hardware processor, automatically determining, based on severity of at least one identified symptom, a listening dosage comprising a duration specifying how long to output each selected audio program, and a frequency specifying how many times to output each selected audio program within a period of time;
- at the hardware processor, automatically configuring each selected audio program to include, within the audio program, a degree of periodic repetition of at least one musical attribute selected from the group consisting of a musical phrase, a chord progression, and a melody, to address the at least one anxiety-related symptom identified in the received input; and
- at an audio output device, automatically outputting, for the determined duration and according to the specified frequency, the selected at least one of the audio programs to mitigate severity of at least one identified anxiety-related symptom;
- wherein automatically outputting at least one of the audio programs comprises:
- automatically commencing output of the audio program based on the frequency specified by the listening dosage;
- automatically initiating a duration timer based on the duration specified by the listening dosage; and
- upon expiration of the duration timer, automatically stopping output of the audio program, so as to limit the listener's exposure to the audio program to the duration specified by the listening dosage.

14. The method of claim 13, wherein each of the audio programs comprises a musical composition.

15. The method of claim 14, wherein each musical composition comprises a plurality of audio elements, comprising at least one selected from the group consisting of:
- a phrase that repeats throughout the musical composition;
- a plurality of arrangements, each introduced in succession;
- an instrumentation of soft tones introduced in succession; and
- a field recording element;
- and wherein each musical composition comprises at least one selected from the group consisting of:
- a plurality of audio elements disposed to form a melody;
- a plurality of audio elements that are mixed to emphasize solfeggio frequencies;
- a plurality of audio elements adapted to cause moving stereo imaging; and
- a tempo between 40 and 65 beats per minute.

16. The method of claim 14, wherein:
- automatically selecting at least one of the audio programs for output by the audio output device comprises:
- comparing severity of anxiety-related symptoms indicated in the metadata assigned to the audio programs with severity of at least one anxiety-related symptom identified in the received input; and
- selecting at least one musical composition having assigned metadata indicating severity of least one anxiety-related symptom identified in the received input; and
- automatically outputting the at least one audio program comprises automatically outputting the selected at least one musical composition.

17. The method of claim 14, wherein:
- automatically selecting at least one of the audio programs for output by the audio output device comprises automatically generating at least one musical composition adapted to mitigate severity of at least one anxiety-related symptom identified in the input; and automatically outputting the at least one audio program comprises automatically outputting the generated at least one musical composition.

18. The method of claim 13, further comprising at least one selected from the group consisting of:
   automatically detecting at least one physical indicator of severity of at least one anxiety-related symptom being experienced by the listener; and
   receiving a signal from a wearable device indicating severity of at least one anxiety-related symptom being experienced by the listener.

19. The method of claim 13, further comprising:
   at the hardware processor, automatically determining a score based on the input received in response to the prompts of the survey;
   and wherein:
   automatically assessing severity of at least one anxiety-related symptom being experienced by the listener comprises automatically assessing severity of at least one anxiety-related symptom based on the determined score.

20. The method of claim 13, wherein:
   automatically outputting at least one of the audio programs comprises automatically initiating a reminder timer based on the specified frequency; and
   automatically commencing output of the audio program based on the frequency specified by the listening dosage comprises automatically commencing output of the audio program upon expiration of the reminder timer, so as to output the audio program according to the specified frequency.

21. The method of claim 13, further comprising:
   at a visual output device, automatically outputting a visual relaxation program concurrently with the audio program.

22. A non-transitory computer-readable medium for automatically generating restorative music to mitigate symptoms experienced by a listener, comprising instructions stored thereon, that when performed by a hardware processor, perform the steps of:
   for each of a plurality of audio programs, automatically assigning metadata indicating severity of at least one anxiety-related symptom the audio program is able to mitigate;
   causing an electronic storage device to store the metadata;
   causing an output device to output a survey comprising a plurality of prompts for identifying at least one anxiety-related symptom being experienced by the listener, and for assessing severity of each identified symptom;
   causing a user input device to receive input in response to the prompts of the survey;
   based on the received input, automatically identifying at least one anxiety-related symptom being experienced by the listener, and automatically assessing severity of each identified symptom;
   automatically selecting at least one of the audio programs, based on a match between severity of at least one anxiety-related symptom identified in the received input and severity of at least one anxiety-related symptom indicated in the stored metadata for the at least one audio program;
   automatically determining, based on severity of at least one identified symptom, a listening dosage comprising a duration specifying how long to output each selected audio program, and a frequency specifying how many times to output each selected audio program within a period of time; and
   automatically configuring each selected audio program to include, within the audio program, a degree of periodic repetition of at least one musical attribute selected from the group consisting of a musical phrase, a chord progression, and a melody, to address the at least one anxiety-related symptom identified in the received input; and
   causing an audio output device to automatically output, for the determined duration and according to the specified frequency, the selected at least one of the audio programs to mitigate severity of at least one identified anxiety-related symptom;
   wherein automatically outputting at least one of the audio programs comprises:
   automatically commencing output of the audio program based on the frequency specified by the listening dosage;
   automatically initiating a duration timer based on the duration specified by the listening dosage; and
   upon expiration of the duration timer, automatically stopping output of the audio program, so as to limit the listener's exposure to the audio program to the duration specified by the listening dosage.

23. The non-transitory computer-readable medium of claim 22, further comprising instructions stored thereon, that when performed by the hardware processor, perform at least one step selected from the group consisting of:
   automatically detecting at least one physical indicator of severity of at least one anxiety-related symptom being experienced by the listener; and
   receiving a signal from a wearable device indicating severity of at least one anxiety-related symptom being experienced by the listener.

24. The non-transitory computer-readable medium of claim 22, further comprising instructions stored thereon, that when performed by a hardware processor, perform the step of:
   automatically determining a score based on the input received in response to the prompts of the survey;
   and wherein:
   automatically assessing severity of at least one anxiety-related symptom being experienced by the listener comprises automatically assessing severity of at least one anxiety-related symptom based on the determined score.

25. The non-transitory computer-readable medium of claim 22, wherein:
   automatically outputting at least one of the audio programs comprises automatically initiating a reminder timer based on the specified frequency; and
   automatically commencing output of the audio program based on the frequency specified by the listening dosage comprises automatically commencing output of the audio program upon expiration of the reminder timer, so as to output the audio program according to the specified frequency.

26. The non-transitory computer-readable medium of claim 22, wherein each of the audio programs comprises a musical composition.

27. The non-transitory computer-readable medium of claim 26, wherein each musical composition comprises a plurality of audio elements, comprising at least one selected from the group consisting of:
- a phrase that repeats throughout the musical composition;
- a plurality of arrangements, each introduced in succession;
- an instrumentation of soft tones introduced in succession; and
- a field recording element;

and wherein each musical composition comprises at least one selected from the group consisting of:
- a plurality of audio elements disposed to form a melody;
- a plurality of audio elements that are mixed to emphasize solfeggio frequencies;
- a plurality of audio elements adapted to cause moving stereo imaging; and
- a tempo between 40 and 65 beats per minute.

28. The non-transitory computer-readable medium of claim 26, wherein each musical composition comprises at least one selected from the group consisting of:
- a plurality of audio elements disposed to form a melody;
- a plurality of audio elements that are mixed to emphasize solfeggio frequencies;
- a plurality of audio elements adapted to cause moving stereo imaging; and
- a tempo between 40 and 65 beats per minute.

29. The non-transitory computer-readable medium of claim 26, wherein:
automatically selecting at least one of the audio programs for output by the audio output device comprises:
- comparing severity of anxiety-related symptoms indicated in the metadata assigned to the audio programs with severity of at least one anxiety-related symptom identified in the received input; and
- selecting at least one musical composition having assigned metadata indicating severity of at least one anxiety-related symptom identified in the received input; and causing the audio output device to automatically output the at least one audio program comprises causing the audio output device to automatically output the selected at least one musical composition.

30. The non-transitory computer-readable medium of claim 26, wherein:
automatically selecting at least one of the audio programs for output by the audio output device comprises automatically generating at least one musical composition adapted to mitigate severity of at least one anxiety-related symptom identified in the input; and
causing the audio output device to automatically output the at least one audio program comprises causing the audio output device to automatically output the generated at least one musical composition.

* * * * *